(12) United States Patent
Mao et al.

(10) Patent No.: US 8,361,502 B2
(45) Date of Patent: Jan. 29, 2013

(54) COMPOSITIONS AND METHODS FOR THE EXPANSION AND DIFFERENTIATION OF STEM CELLS

(75) Inventors: Hai-Quan Mao, Baltimore, MD (US);
Kam W. Leong, Durham, NC (US);
Kian-Ngiap Chua, Singapore (SG);
Seeram Ramakrishna, Singapore (SG)

(73) Assignee: The Johns Hopkins University, Baltimore, MD (US)

( * ) Notice: Subject to any disclaimer, the term of this patent is extended or adjusted under 35 U.S.C. 154(b) by 855 days.

(21) Appl. No.: 11/975,492

(22) Filed: Oct. 18, 2007

(65) Prior Publication Data
US 2008/0153163 A1 Jun. 26, 2008

Related U.S. Application Data

(60) Provisional application No. 60/852,598, filed on Oct. 18, 2006.

(51) Int. Cl.
*A61K 9/14* (2006.01)
(52) U.S. Cl. ....................................... 424/484
(58) Field of Classification Search ........................ None
See application file for complete search history.

(56) References Cited

U.S. PATENT DOCUMENTS

2006/0204539 A1* 9/2006 Atala et al. ................... 424/423
2006/0264140 A1* 11/2006 Andrady et al. .............. 442/341

OTHER PUBLICATIONS

Chua et al, Stable immobilization of rat hepatocyte spheroids on galactosylated nanofiber scaffold, Biomaterials, 2005, 26, 2537-2547.*
Preparation and Morphology of PES Nanofibers by Electrospinning, Journal of Yunnan University, 2005, 27, 231-233.*
English translation of "Preparation and Morphology of PES Nanofibers by Electrospinning, Journal of Yunnan University, 2005, 27, 231-233", Aug. 2011.*
http://www.merriam-webster.com/dictionary/graft?show=1 &t=1314355259, accessed Aug. 26, 2011.*
Chua Kn et al. "Surface-aminated electrospun nanofibers enhance adhesion and expansion of human umbilical cord blood hematopoietic stem/progenitor cells." Biomaterials. Dec. 2006;27(36):6043-51.

* cited by examiner

*Primary Examiner* — Paul Dickinson
(74) *Attorney, Agent, or Firm* — Edwards Wildman Palmer LLP; Peter F. Corless; Melissa Hunter-Ensor, Esq.

(57) ABSTRACT

The instant invention provides methods and compositions for the expansion and differentiation of stem cells.

23 Claims, 17 Drawing Sheets

COMPOSITIONS AND METHODS FOR THE EXPANSION AND DIFFERENTIATION OF STEM CELLS

RELATED APPLICATIONS

This application claims the benefit of U.S. Provisional Application No. 60/852,598, filed Oct. 18, 2007, the entire contents of which are hereby incorporated herein by reference.

BACKGROUND OF THE INVENTION

Stem cells have the potential to cure numerous disease and disorders. However, the sources of stem cells are limited. A representative example of the problem with obtaining stem cells is illustrated by human umbilical cord blood (UCB) hematopoietic stem/progenitor cells (HSPCs). HSPCs are multipotent cells that have the capacity to self-renew and differentiate into all mature blood cell types. However, the low number of HSPCs obtainable from umbilical cords due to the small volume of blood collected limits direct UCB HSPC transplantation treatments to pediatric patients. Therefore, several approaches have been explored to expand HSPCs in ex vivo expansion systems, so that UCB could serve as a readily viable source of transplantable HSPCs for adult patients suffering from a variety of disorders.

In conventional ex vivo expansion culture, HSPCs are generally regarded as suspension cells and numerous protocols implement HSPC suspension cultures in flasks or bags in the presence of various combinations of early acting cytokines. These protocols do not produce enough stem cells to be of clinical significance. Similar problems exist with the expansion of other types of stem cells.

Accordingly, the need exists for improved methods and compositions for the expansion and differentiation of stem cells.

SUMMARY OF THE INVENTION

The instant inventors have discovered novel and improved compositions and methods for the expansion and differentiation of stem cells. In one aspect, the inventors have found a way to mimic the natural environment where stem cells exist. For example, the inventors have found a way to mimic the natural bone marrow environment wherein HSPC exist naturally.

Accordingly, in one aspect, the invention provides nanofiber compositions for the expansion or differentiation of stem cells comprising one or more electrospun polymers. In a related embodiment, an additional polymer is grafted onto the one or more electrospun polymers. In a related embodiment, the grafted polymer is derivatized. In one embodiment the polymer is derivatized with carboxylic, hydroxyl or amino groups. In another embodiment, the polymer is derivatized with a positively charged moiety. In another embodiment, the polymer is derivatized with peptide or polypeptide, e.g., a cell adhesion peptide or polypeptide or heparin.

In another embodiment, the polymer or polymers are selected from the group consisting synthetic polymers, natural polymers, protein engineered biopolymers or combinations thereof.

In a particular embodiment, the grafted polymer is poly(acrylic acid) (PAAc). In another particular embodiment, the electrospun polymers comprises polyethersulfone (PES).

In another embodiment, the composition of the invention has a spacer between the grafted nanofiber and the derivatized moiety. Exemplary spacers are ethylene, butylenes or hexylene moieties.

In particular embodiments of the invention, the compositions of the invention are useful for expanding or differentiating hematopoietic stem/progenitor cells, or neural stem cells, embryonic stem cells.

In other embodiments, the grafted electrospun nanofiber compositions of the invention have a diameter between 10 nm to 10 µm, preferably between 100-700 nm. In a specific embodiment, the grafted electrospun nanofiber composition of the invention comprises poly(acrylic acid) grafted on to a polyethersulfone core. In a further embodiment, this composition is derivatized. In particular embodiments the composition is derivatized by amination, with peptides or polypeptides, e.g., laminin, heparin, or cell adhesion peptides or polypeptides.

In another embodiment, the electrospun composition comprises spacers between the electrospun fiber and the derivatized moiety. In exemplary embodiments the spacers comprise ethylene, butylene or hexylene moieties.

In one particular embodiment, the grafted electrospun nanofiber composition comprises poly(acrylic acid) grafted on to a polyethersulfone core, wherein the poly(acrylic acid) is aminated. In particular embodiments the electrospun fiber compositions are useful for the expansion or differentiation of stem cells, e.g., hematopoietic stem/progenitor cells, neural stem cells, or embryonic stem cells. In certain embodiments of the invention, the electrospun nanofiber composition of the invention has randomly oriented fibers. In alternate embodiments, the electrospun nanofiber composition of the invention has aligned fibers. In further embodiments, the grafted electrospun is produced uniaxial electrospinning, coaxial, or multiaxial electrospinning.

The invention further provides methods for the expansion of a stem cell population comprising by a stem cell population with the grafted electrospun nanofiber composition described herein thereby expanding the stem cell population. Specifically, the invention further provides methods for expanding or differentiating hematopoietic stem/progenitor cell, embryonic cells, or neural cells.

The invention further provides methods of producing erythroid committed cells by contacting a hematopoietic stem/progenitor cell population with the grafted electrospun nanofiber compositions of the invention; isolating the cells growing in suspension after a time sufficient for expansion and differentiation of the cell population, thereby producing erythroid committed cells.

In another aspect the invention further provides kits for the expansion or differentiation of a stem cell population comprising the grafted electrospun nanofiber compositions of the invention and instructions for use.

Data shown are means±SD of 3-8 independent experiments, each conducted in triplicates. Unmodified, carboxylated, hydroxylated and aminated conditions were designated as "unmod.", "COOH", "OH" and "NH2" respectively.

Figure 3:
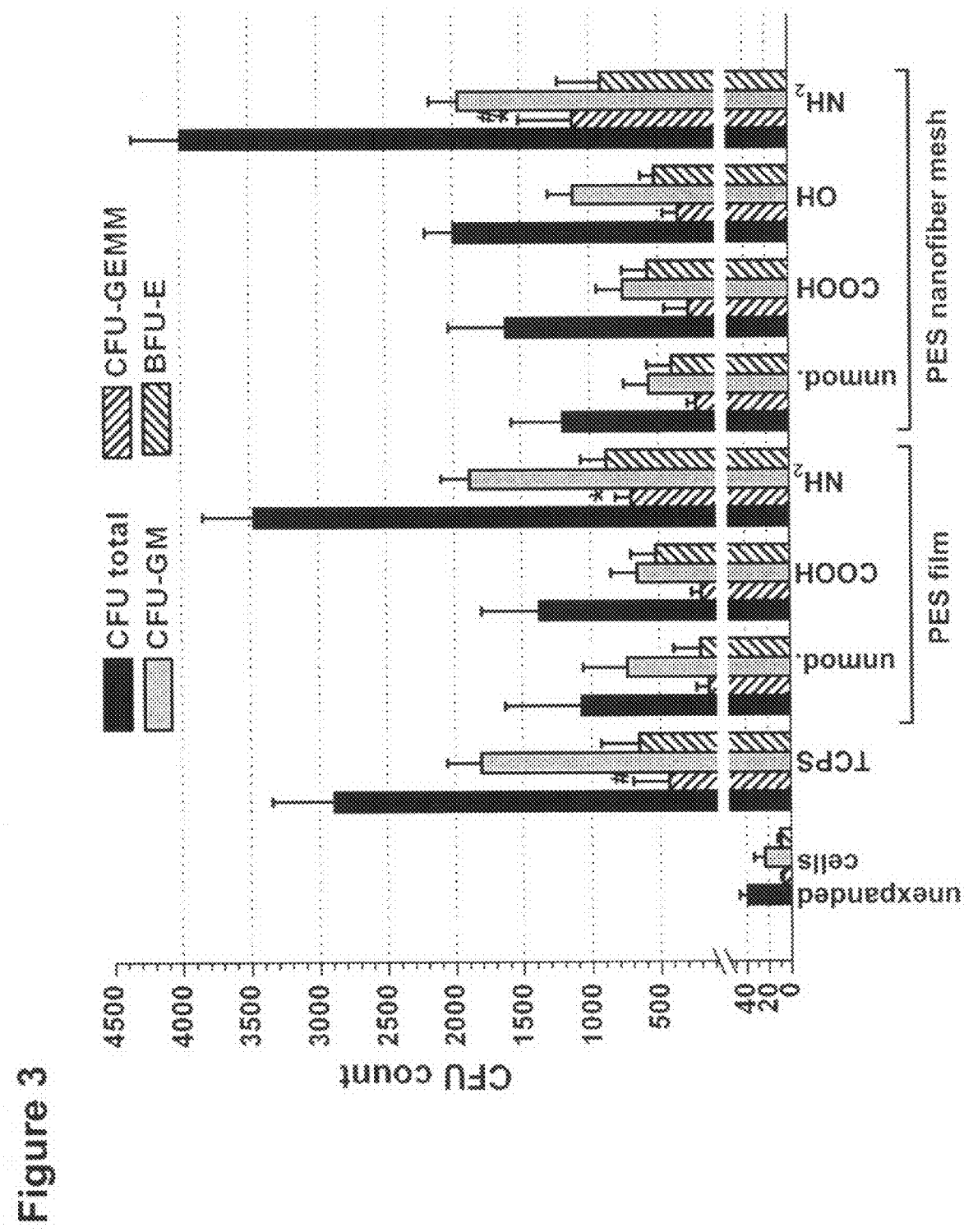

FIG. 3 shows CFU counts generated after 14 days of culture, using the cells from the 10-day expansion cultures on various substrates and from the unexpanded HSPCs. Data are normalized to CFU number per 100 initial unexpanded HSPCs. Data shown are the mean±SD of 3-8 experiments, each conducted in triplicates. *, # denotes statistical significance of p<0.05. Unmodified, carboxylated, hydroxylated and aminated conditions were designated as "unmod.", "COOH", "OH" and "NH2" respectively.

Figure 4:
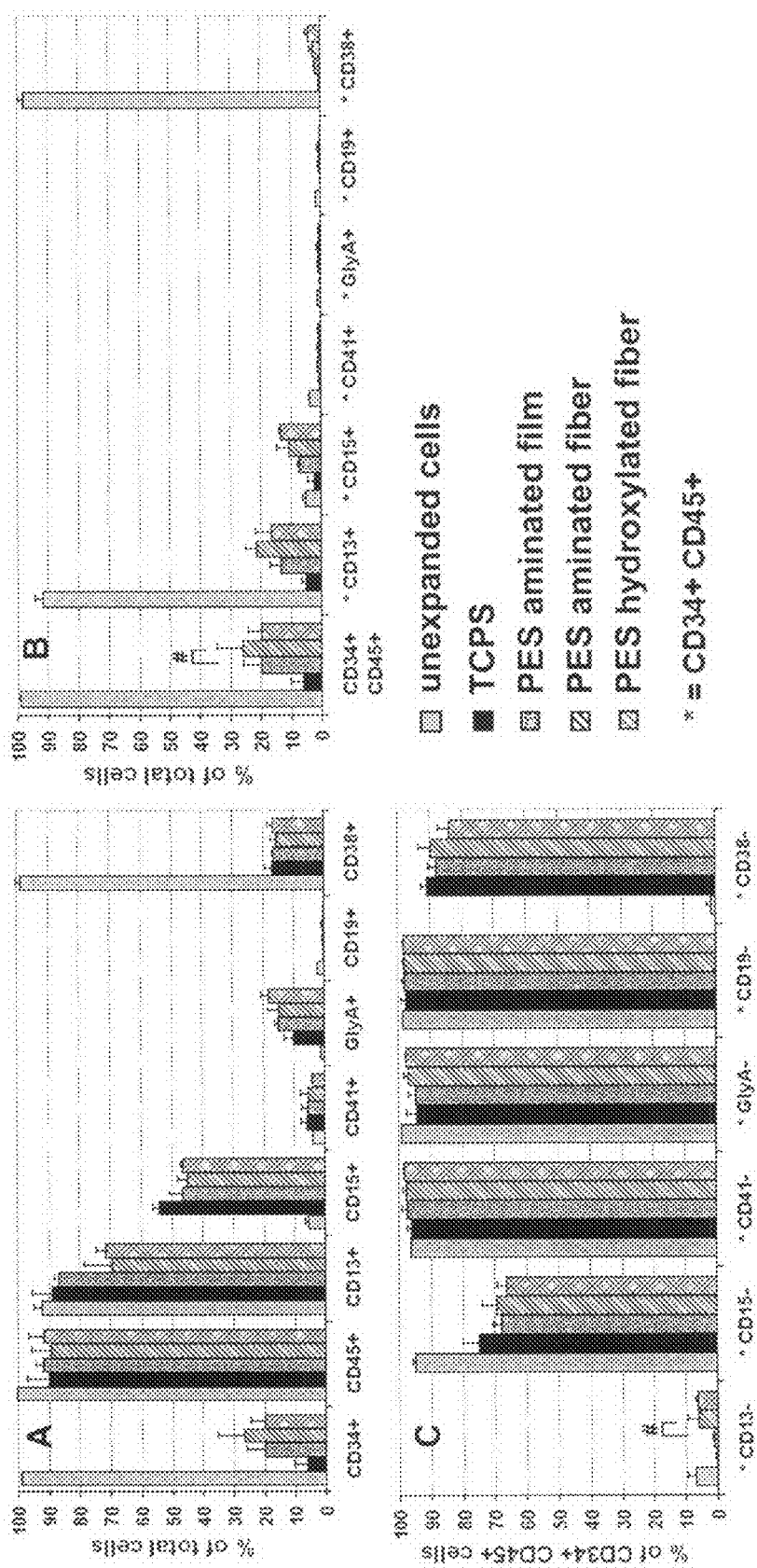

FIG. 4 (A-C) shows surface antigen expression on cells after 10-day ex vivo expansion on different substrates. (A) Percentage of total cells that are CDX+. (B) Percentage of total cells that are CD34+CD45+CDX+. (C) Percentage of the CD34+CD45+ cell population that are CD34+CD45+CDX−. "CDX" represents CD34, CD45, CD13, CD15, CD41, GlyA, CD19 or CD38. Data shown are mean±SD of 3-6 experiments, each conducted in duplicates. # denotes statistical significance of p<0.05.

Figure 5:
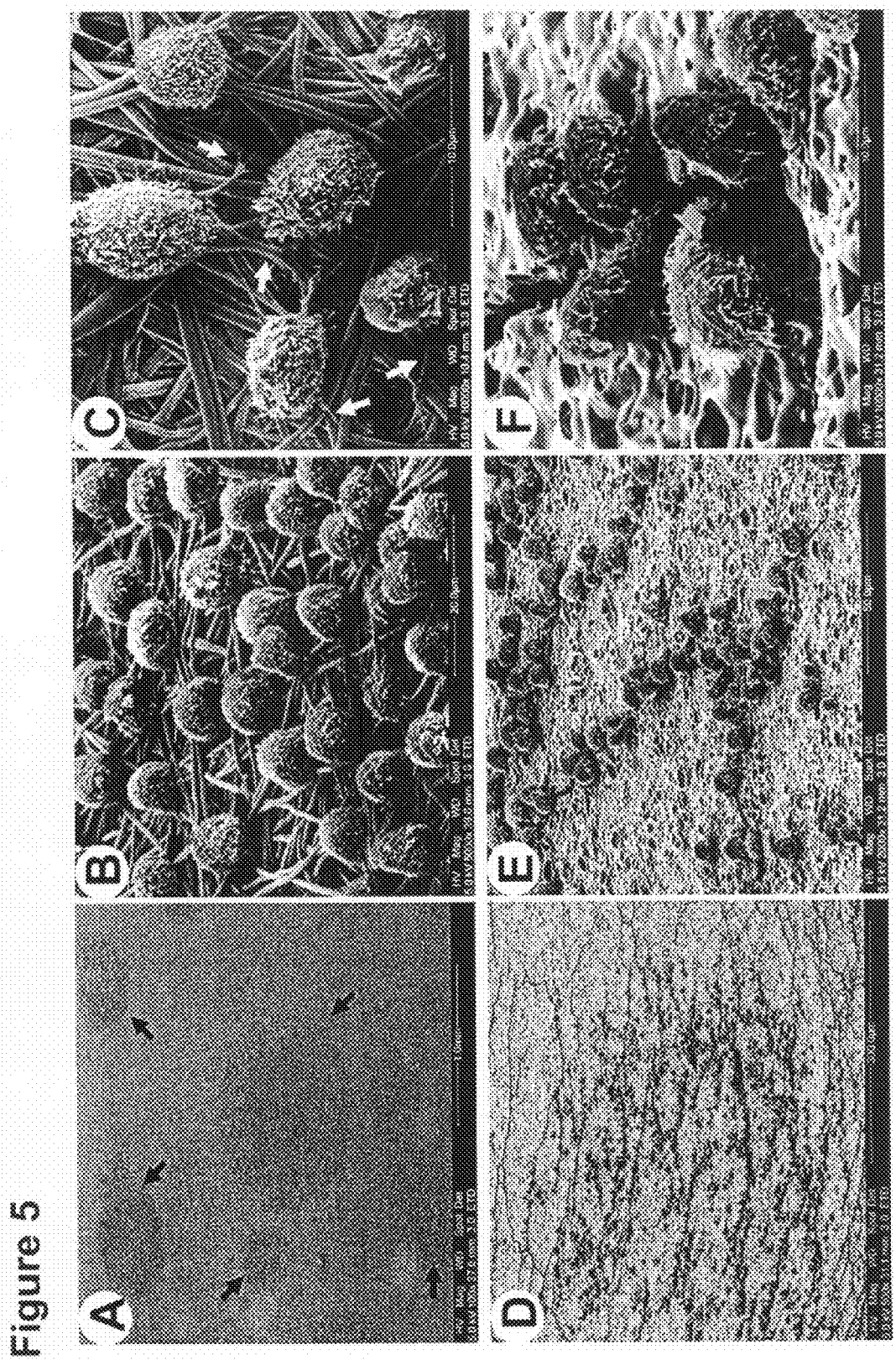

FIG. 5 (A-F) shows SEM images of human cord blood HSPCs after a 10-day expansion culture on aminated PES nanofiber mesh (A-C) and on aminated PES film (D-F) at various magnifications. Abundant distinct, circular cell colonies are evident on the aminated nanofiber scaffold (black arrows). Filopodia extend from the cells and interact with the aminated nanofibers (white arrows). On aminated film, fewer cells are adherent without colony formation; cells appear to attach along cracks.

Figure 6:
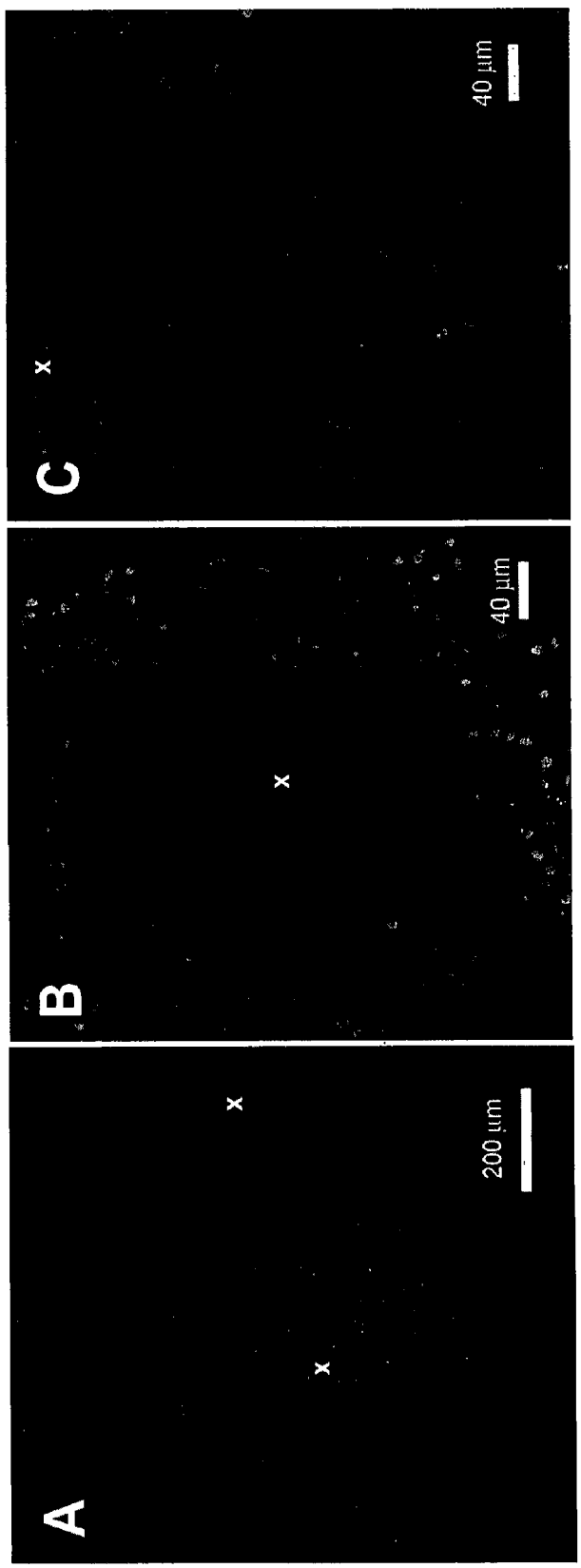

FIG. 6 (A-C) shows confocal laser microscopy images of human cord blood HSPCs after a 10-day expansion culture on aminated PES nanofiber mesh. Green indicates Syto16 nuclear staining and red indicates CD34-PE staining. (A) Fluorescent image of two representative cell colonies stained with Syto16. (B, C) CD34+ cells can be found on these cell colonies and they appear to concentrate around the periphery of the colonies. "x" denotes the approximate center of the cell colony.

Figure 7:
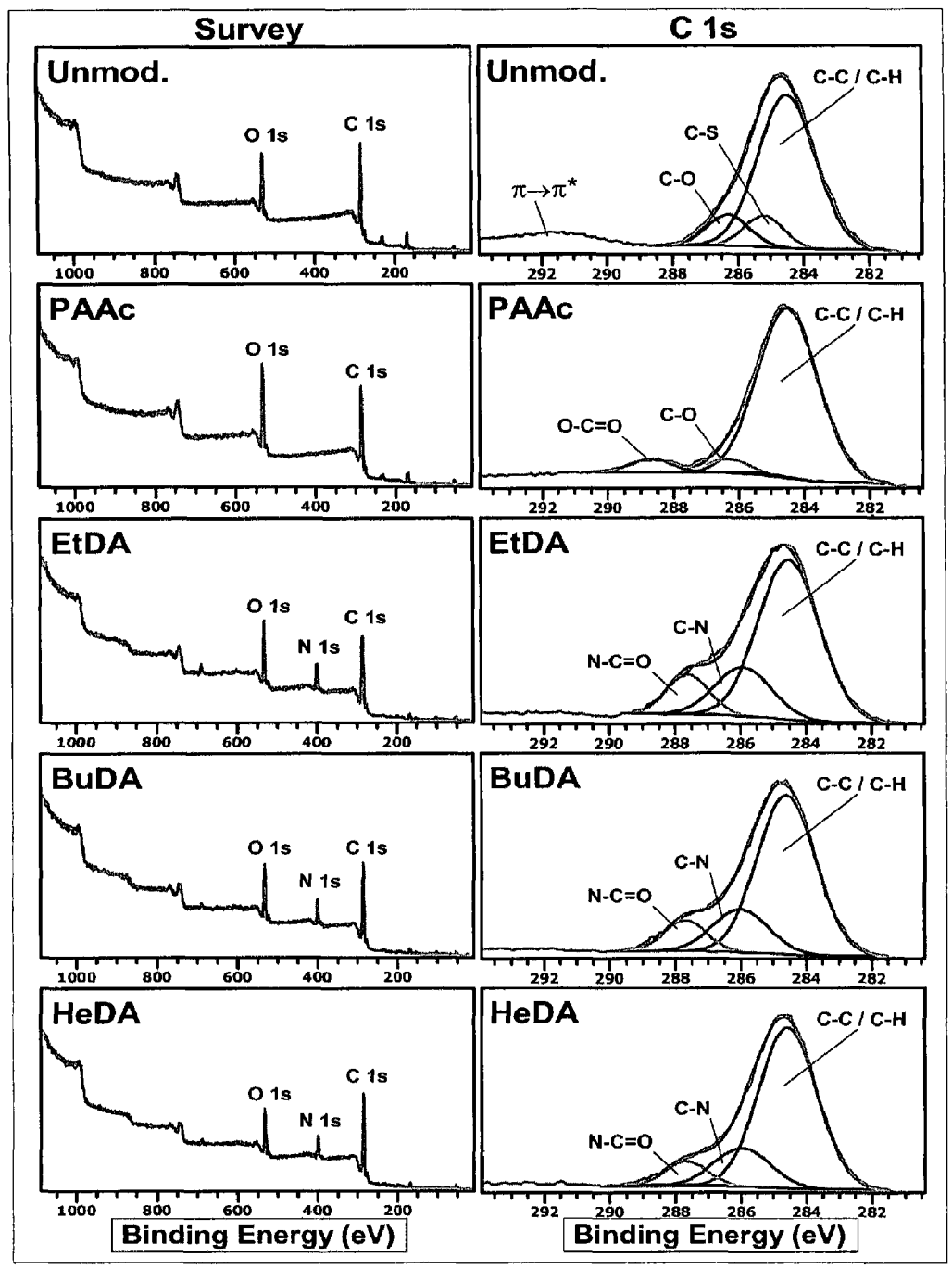

FIG. 7 shows the XPS spectra of various PES nanofiber scaffolds.

Figure 8:
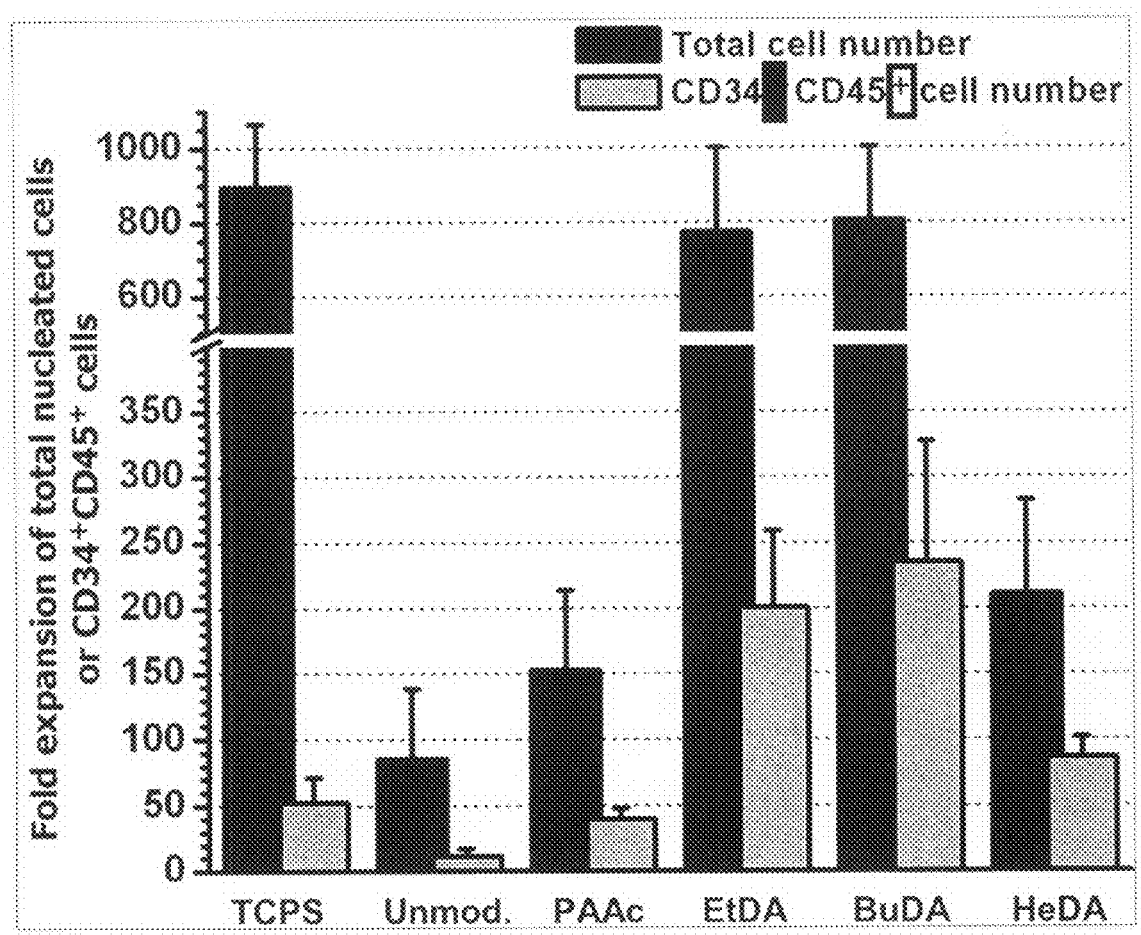

FIG. 8 shows fold expansion of total nucleated cells and CD34+CD45+ cells following a 10-day culture of human cord blood HSPCs on TCPS and various PES nanofiber scaffolds. Bars represent means±SD of 3-8 independent experiments, each conducted in triplicates.

Figure 9:
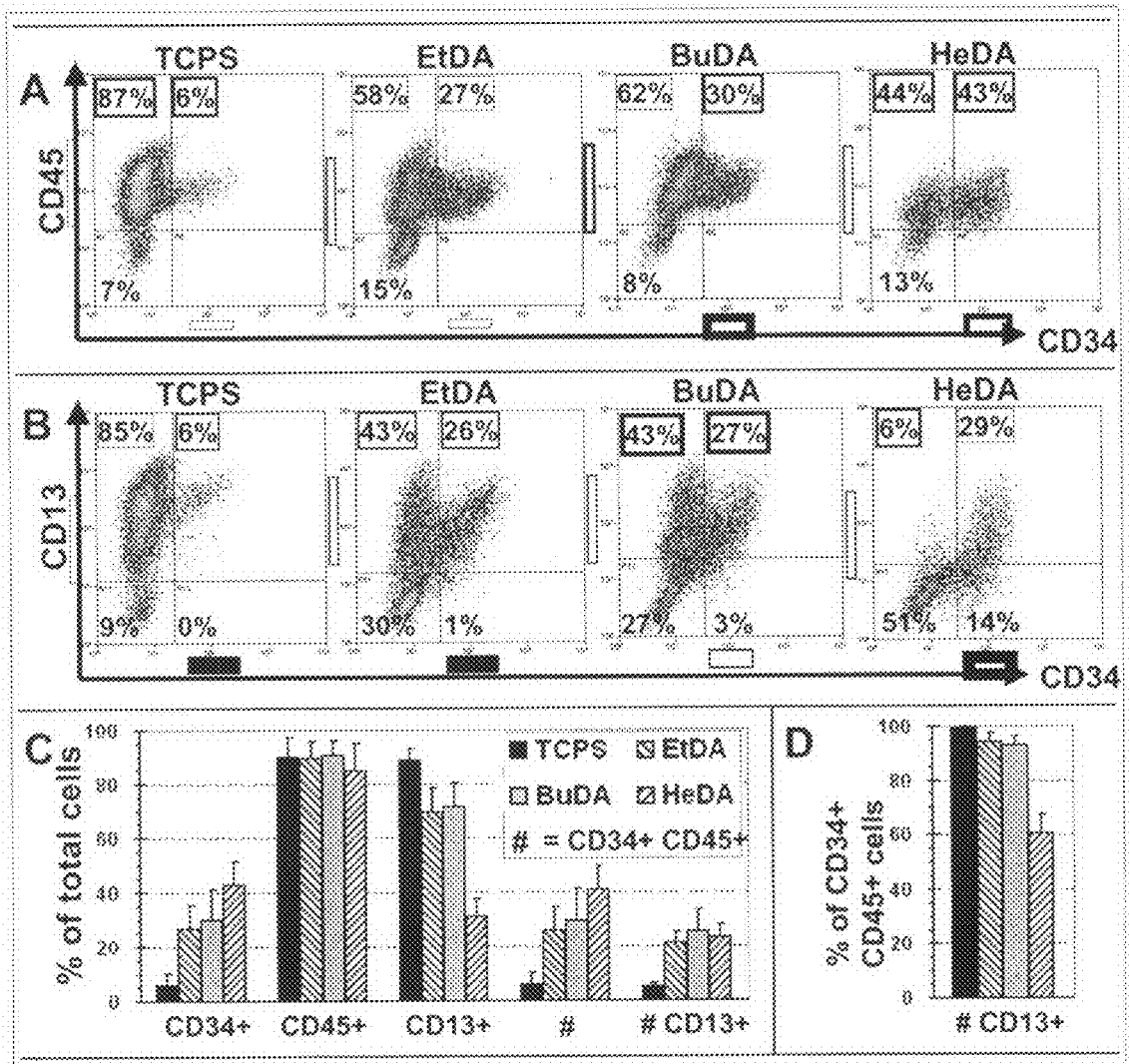

FIG. 9 (A-D) shows representative FACS profiles (A, B) and surface marker expression summary (C, D) of expanded cells after 10-day HSPC expansion cultures on TCPS, and EtDA, BuDA and HeDA nanofiber scaffolds. (A) CD45 vs. CD34. (B) CD13 vs. CD34. (C) Percentage of total cells expressing one or multiple CD markers. (D) Percentage of the CD34+CD45+ cell population that are CD13+. Bars represent means±SD of 5-8 experiments, each conducted in duplicates.

Figure 10:
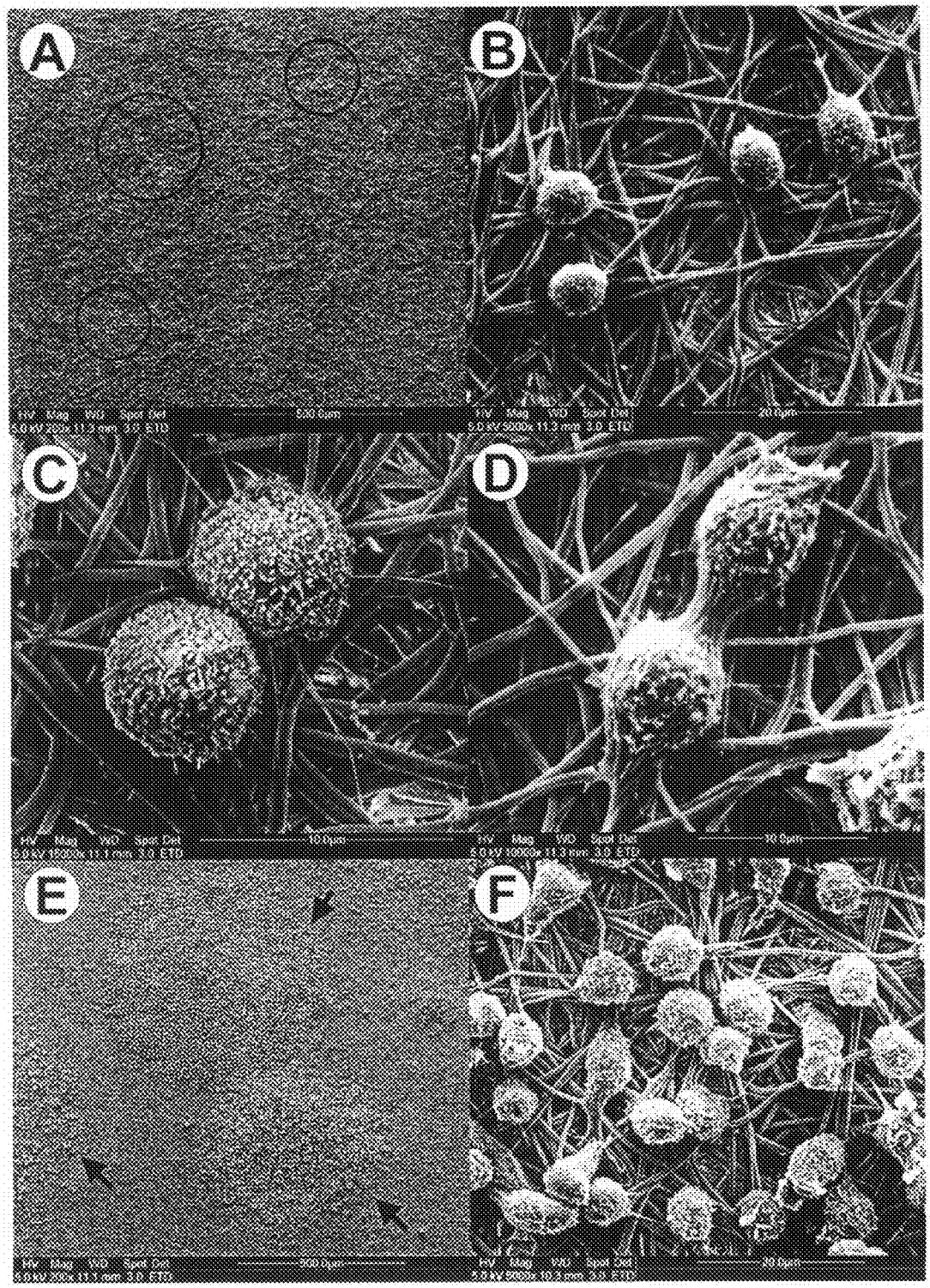

FIG. 10 (A-F) shows SEM images of HSPCs after (A-D) 3-day and (E, F) 8-day cultures on PES BuDA nanofiber mesh at various magnifications. (A, B) Pockets of adherent HSPCs were observed (white circles) proliferating on the aminated nanofiber surface on day 3. (C) Cells exhibited numerous filopodia which were interacting with the aminated nanofibers. (D) Cell division was observed occurring on the nanofiber surface. (E, F) HSPCs proliferated to form circular colonies (black arrows) on the nanofiber surface, shown on day 8.

Figure 11:
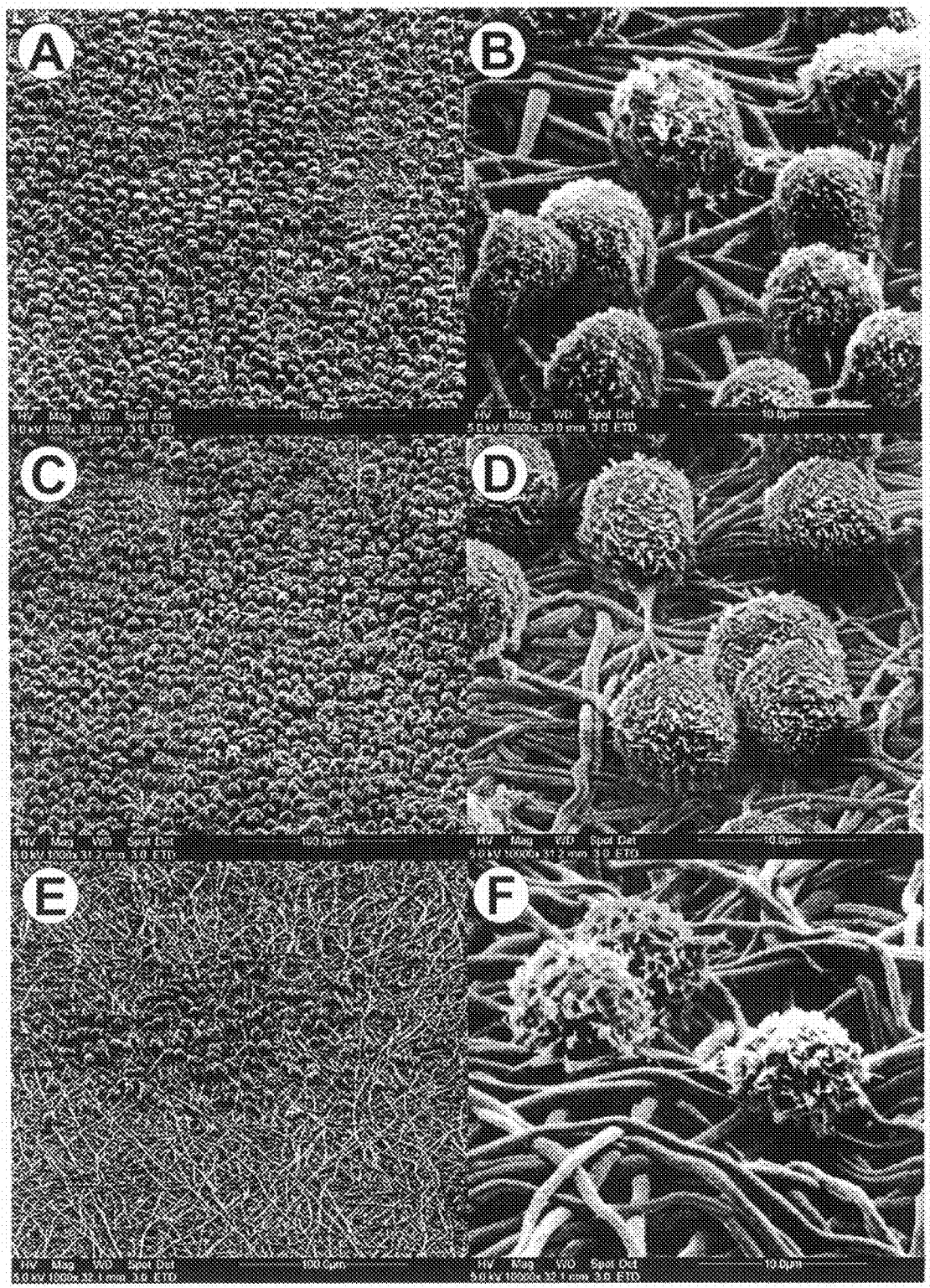

FIG. 11 (A-F) shows SEM images of adherent cell colonies after 10 days of expansion on arninated PES nanofibers conjugated with EtDA (A, B), BuDA (C, D) and HeDA (E, F), respectively. Colonies of densely packed adherent cells were observed on EtDA and BuDA nanofiber surfaces. On HeDA nanofiber surfaces, adherent cells were sparsely located.

Figure 12:
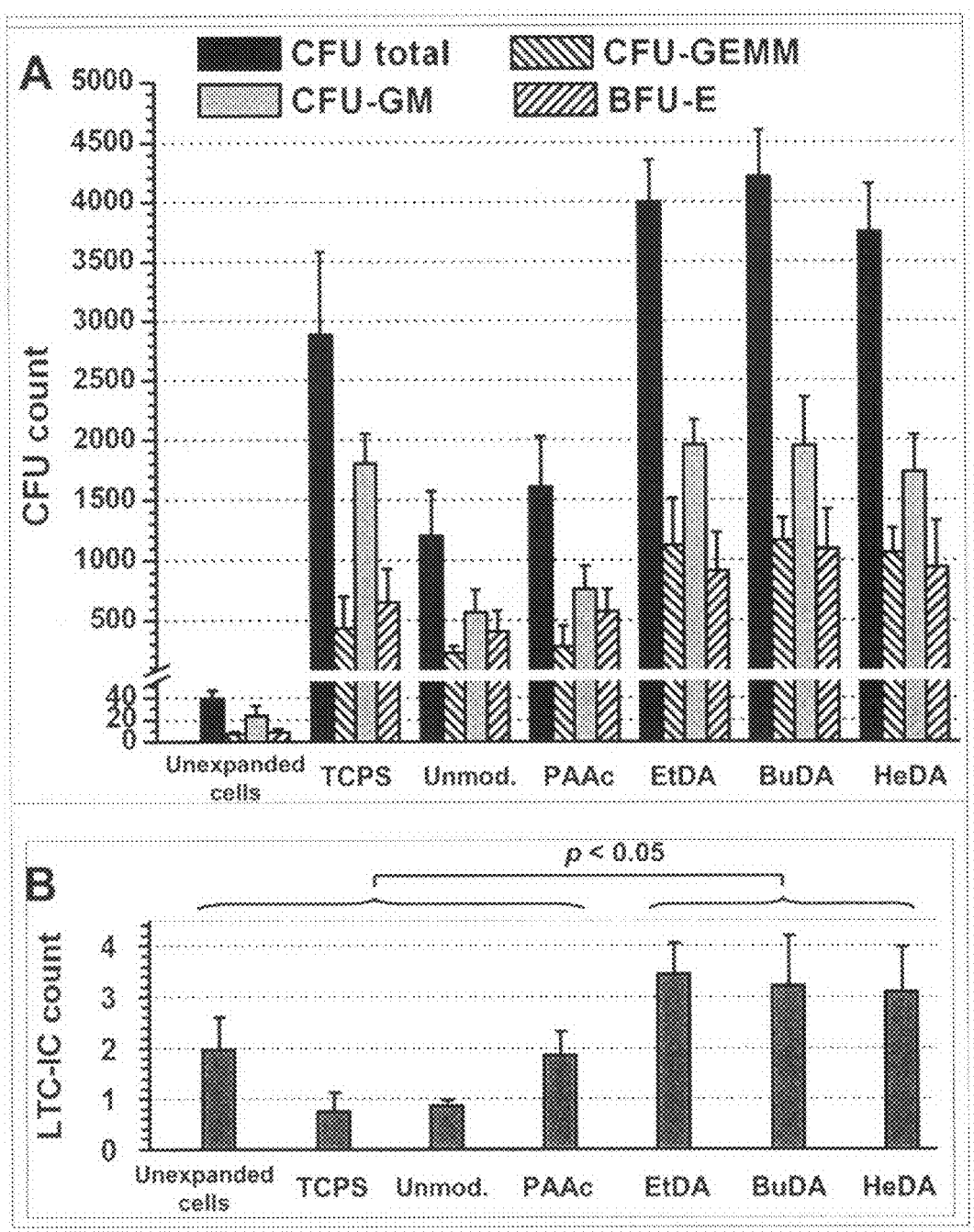

FIGS. 12 (A and B) shows CFU counts after 14 days of culture; and (B) LTC-IC counts after 7 weeks of culture, from unexpanded HSPCs and from expanded cells after 10-day HSPC expansion cultures on TCPS and various PES nanofiber scaffolds, normalized to CFU or LTC-IC per 100 initial unexpanded HSPCs. (A) Bars represent means±SD of 3-8 experiments, each conducted in triplicates. (B) Bars represent means±SD of 2 experiments, each conducted in triplicates.

Figure 13:
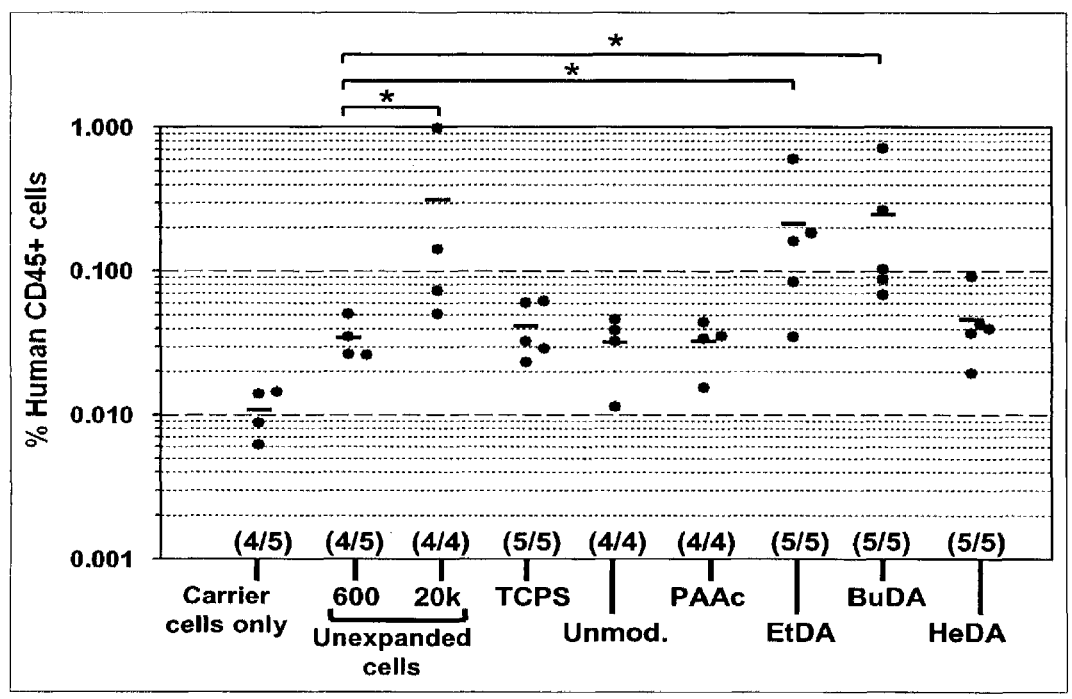

FIG. 13 shows engraftment efficiency of human CD45+ cells in bone marrow of sub-lethally irradiated NOD/SCID mice transplanted with unexpanded HSPCs, expanded cells derived from 600 CD34+ cells following 10-day expansion culture on TCPS and various PES nanofiber scaffolds, and irradiated carrier cells alone. Numbers in parentheses indicate mice survival in the different experimental groups. * indicates p<0.05.

Figure 14:
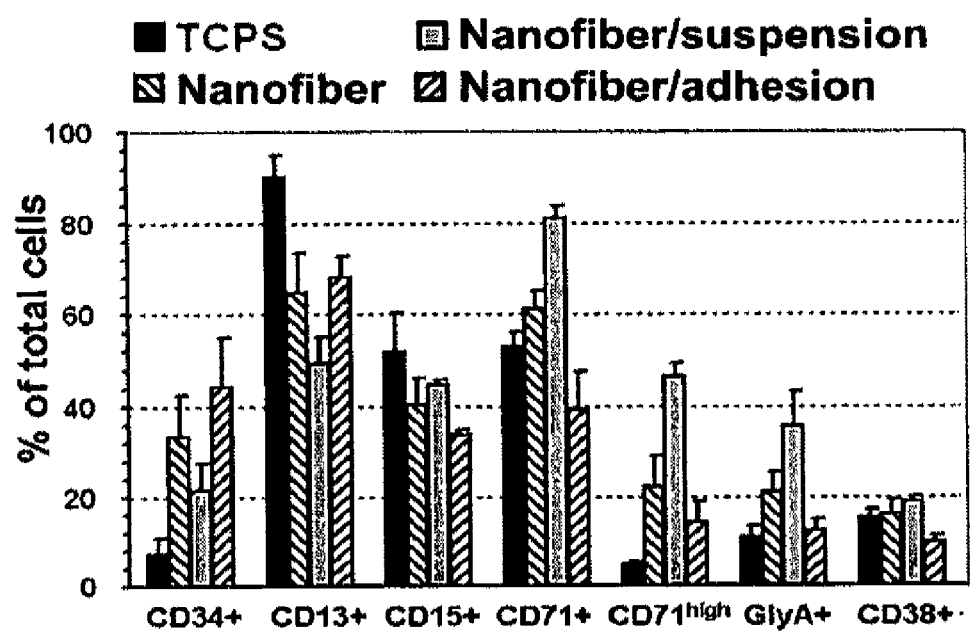

FIG. 14 shows surface marker expression on cells after 10-day ex vivo expansion on TCPS, nanofibers, and suspension and adhesion fractions expanded on nanofibers. Data shown are mean±SD of 3 different experiments, each conducted in duplicates.

Figure 15:
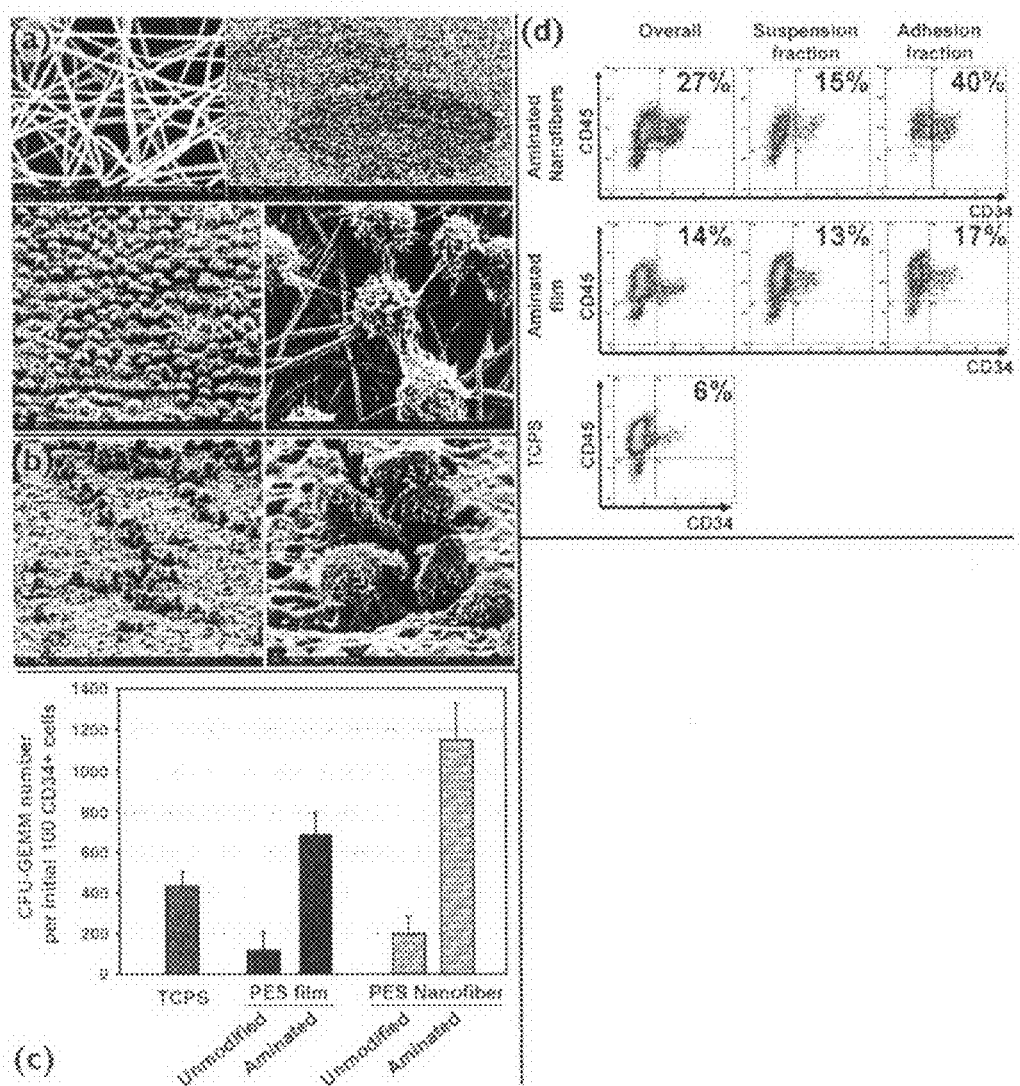

FIG. 15 (A-D) are four panels. Panel (A) shows SEM images showing that human cord blood HSCs cultured on aminated nanofibers formed circular colonies after 10 days of expansion, whereas random adherent cells were found at the cracks on 2-D film (B). Functionalized PES fibers have an average diameter of 529 nm and the average surface amino group concentration was 55 nmol/cm$^2$. (C). Ami-nated nanofibers promoted the expansion of CFU-GEMM colony forming cells (CFU-GEMM: colony-forming unit-granulocyte, erythrocyte, monocyte & megakaryocyte). (D). Phenotypic comparison between adherent and suspension populations of the cells expanded on aminated PES nanofiber scaffolds, film and TCPS.

Figure 16:
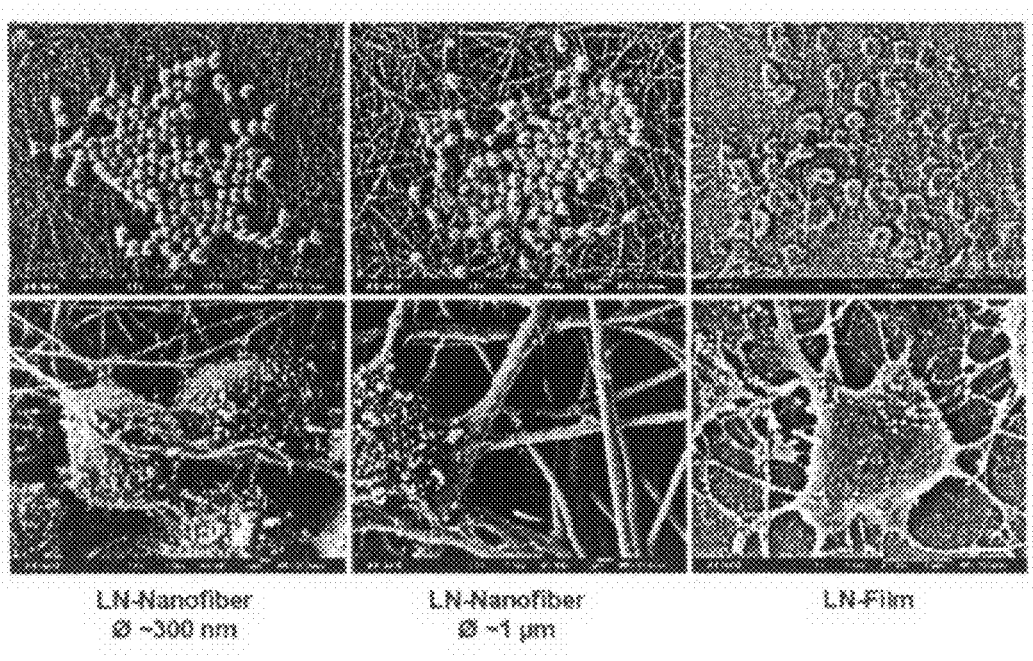

FIG. 16 shows rat NSCs adhered to LN-coated PES nanofibers and film following five days of culture. Cell processed conformed to nanofibers with two different diameters (~300 nm, left column), ~1 μm, middle column) and maintained more rounded morpho-logy, in contrast to a flattened morphology on LN-film (right).

Figure 17:
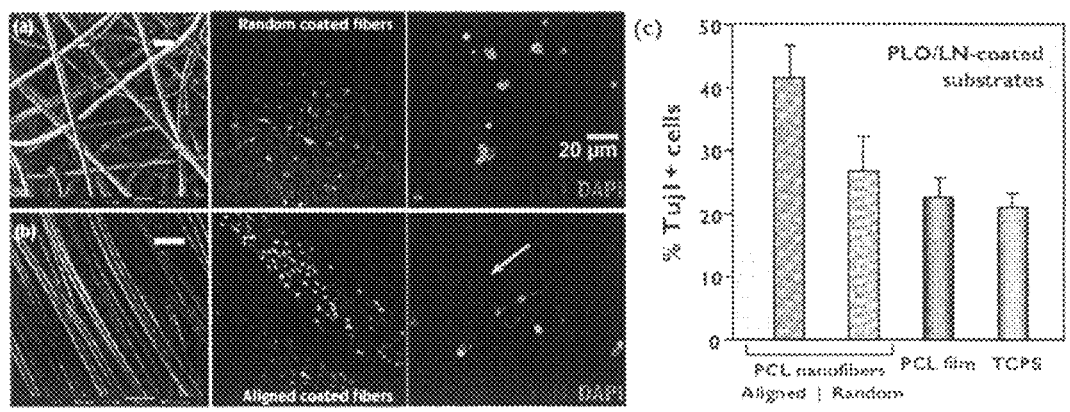

FIG. 17 (A-C) shows rat adult NSCs differentiated on random and aligned LN-coated polycaprolactone (PCL) nanofibers, and LN-coated PCL film and TCPS dish. The average diameter of the fibers is 250 nm. NSCs were cultured in the presence of 0.5% fetal bovine serum and 0.5 μM retinoic acid. Differentiated cells formed extended long processes along fiber axis. Fibers provided guidance cue for process extension and outgrowth. Arrow in (B) indicates the axis of aligned fibers. (C). NSCs differentiated on aligned nanofibers showed higher percentage of neuronal commitment (Tuj1+) than that on random fibers and 2-D substrates.

DETAILED DESCRIPTION

The instant invention is directed to novel methods and compositions for the expansion and differentiation of stem cells. The following terms will help in defining the invention.

As used herein, the term "stem cell" refers to self-renewing cells that are capable of giving rise to phenotypically and genotypically identical daughters as well as at least one other final cell type (e.g., terminally differentiated cells). Stem cells include, but are not limited to, hematopoietic stem cells; neural crest stem cells; embryonic stem cells; mesenchymal stem cells; mesodermal stem cells; stromal stem cells, pulmonary epithelial stem cells, hepatic stem cells, and other stem cells.

"Stem cells" can be generally defined as undifferentiated cells having the ability to differentiate into specialized cells or polyfunctional cells, as well as having the ability to self-replicate, allowing repeated generation of cells identical to themselves. Unique stem cells are found in each tissue and cell type, and for example, blood cells such as erythrocytes, lymphocytes and megakaryocytes are produced via progenitor cells derived from stem cells known as "hematopoietic stem cells", while skeletal muscle cells are produced from stem cells/precursor cells known as "satellite cells" and "myoblasts". Additional types that have been identified to date include neural stem cells that are found in neural tissue such as the brain and spinal cord and produce neurons and glial cells, epidermal stem cells that produce epidermal cells and hair follicle cells, oval cells (hepatic stem cells) that produce hepatocytes and bile duct cells, and cardiac stem cells that produce cardiomyocytes. Stem cells can be measured by as described herein. For example, marker produced by stem cells can be monitored to determine the number of stem cells in a sample.

Embryonic stem cells (ES cells) are derived from totipotent cells from early mammalian embryo and are capable of unlimited undifferentiated proliferation in vitro (Evans and Kaufman, Nature, 292:154 (1981); Martin, G., Proc. Natl. Acad. Sci. USA, 78:7634 (1981). ES cells can differentiate into any cell type in vivo (Evans et al., Nature, 292:154-156 (1981); Bradley, et al., Nature, 309:255-256 (1984)), and into a variety of cells in vitro (Doetschman, et al., J. Embryol. Exp. Morph., 87:27-45 (1985); Wobus, et al., Biomed. Biochim. Acta, 47:965-973 (1988); Robbins, et al., J. Biol. Chem., 265:11905-11909 (1990)). Non-human primate and human embryonic stem cell lines have been established (see, e.g., Thomson and Marshall, Curr Top Dev Biol, 38:133-65 (1998); Thomson et al., Proc Natl Acad Sci USA, 92:7844-7848 (1995); and Thomson et al., Science, 282:1145-1147 (1998)). Primate embryonic stem cells are described, for example, in U.S. Pat. No. 5,843,780 issued on Dec. 1, 1998. Monkey-origin embryonic stem cells are disclosed in U.S. Patent Application Publication No. 2003/0157710 A1, published on Aug. 21, 2003.

As used herein, the "hematopoietic cell" refers to a hematopoietic stem cell and a hematopoietic progenitor cell, which are undifferentiated cells, and excludes differentiated cells, for example, leukocyte (e.g., granulocyte (neutrophil, eosinophil, basophil), monocyte, macrophage, lymphocyte (B cell, T cell, NK cell)), erythrocyte, and platelet. The derivation of the hematopoietic cell is a mammal, e.g., a human.

"Hematopoietic stem cells (HSC)" are cells that give rise to distinct daughter cells, wherein one daughter cell is a replica of the stem cell, while the other daughter cell is a cell that will further proliferate and differentiate into a mature blood cell. HSC are found in blood (adult and umbilical cord) and bone marrow. "Hematopoietic stem cell" refer to a cell possessing both multipotency and renewal function, which is commonly ancestor to leukocyte, erythrocyte, platelet and the like. The hematopoietic stem cell can be CD34+Accordingly, in one aspect, CD34+ cell can be used as the hematopoietic stem cell. In addition to CD34+a plurality of other hematopoietic stem cell markers can be used in combination. Examples of the stem cell marker used in combination with CD34+ include CD38−, DR−, CD45+, CD90+, CD117+, CD123+, and CD133+. Which stem cell marker hematopoietic cell is expressing can be determined by a method known per se such as a method using FACS, and a hematopoietic stem cell expressing a particular stem cell marker can be separated and purified.

The "expansion" refers to increasing the number of what are called undifferentiated cells, which have not differentiated terminally. The expansion of the stem cell can be evaluated by a cell marker analysis (for example, hematopoietic cells can be evaluated by counting the cells corresponding to CD34+ by FACS), quantitative analysis based on the colony assay method, and the like. The phrase "cell expansion" is used herein to describe a process of cell proliferation substantially devoid of cell differentiation. Cells that undergo expansion hence maintain their cell renewal properties and are oftentimes referred to herein as renewable cells, e.g., renewable stem cells.

"Electrospinning", commonly referred to as electrostatic spinning, is a process of producing fibers, with diameters in the range of for example, 10 nm to 100 µM. The process consists of applying a high voltage to a polymer solution or melt to produce a polymer jet. As the jet travels in air, the jet is elongated under repulsive electrostatic force to produce nanofibers. The process has been described in the literature since the 1930. A variety of polymers both natural and synthetic having optimal characteristics have been electrospun under appropriate conditions to produce nanofibers, (see Reneker et al., Nanotechnology, 1996, 7, 216).

The term "grafted electrospun nanofiber composition" refers to a composition comprising a polymer core that is made by electrospinning and further has additional polymers grafted onto the electrospun polymer. In particular embodiments, the grafted polymers reside primarily on the outer surface of the electrospun polymer core.

As used herein the term "differentiation" refers to relatively generalized or specialized changes during development. Cell differentiation of various lineages is a well-documented process and requires no further description herein. As used herein the term differentiation is distinct from maturation which is a process, although some times associated with cell division, in which a specific cell type mature to function and then dies, e.g., via programmed cell death.

As used herein the term "ex-vivo" refers to a process in which cells are removed from a living organism and are propagated outside the organism (e.g., in a test tube). As used herein, the term "ex-vivo", however, does not refer to a process by which cells known to propagate only in-vitro, such as various cell lines (e.g., HL-60, MEL, HeLa, etc.) are cultured.

The invention pertains to methods and compositions for the expansion and differentiation of stem cells. The instant methods rely on the isolation of stem cells from any of a number of sources and the subsequent use of the compositions and methods of the instant invention to expand and/or differentiate these stem cells. Stem cells can be isolated from any of a number of sources and techniques known to those of skill in the art. For example, U.S. Pat. No. 5,061,620 describes a substantially homogeneous human hematopoietic stem cell composition and the manner of obtaining such composition.

The invention pertains to methods and compositions that employ electrospun nanofibers. These electrospun fibers form a core or matrix that is used in the methods and compositions of the invention. The process of electrospinning generally involves the creation of an electrical field at the surface of a liquid. The resulting electrical forces create a jet of liquid which carries electrical charge. The liquid jets may be attracted to other electrically charged objects at a suitable electrical potential. As the jet of liquid elongates and travels, it will harden and dry. The hardening and drying of the elongated jet of liquid may be caused by cooling of the liquid, i.e., where the liquid is normally a solid at room temperature; evaporation of a solvent, e.g., by dehydration, (physically induced hardening); or by a curing mechanism (chemically induced hardening). The produced fibers are collected on a suitably located, oppositely charged target substrate.

The electrospinning apparatus includes an electrodepositing mechanism and a target substrate. The electrodepositing mechanism includes at least one container to hold the solution that is to be electrospun. The container has at least one orifice or nozzle to allow the streaming of the solution from the container. If there are multiple containers, a plurality of nozzles may be used.

One or more pumps (e.g., a syringe pump) used in connection with the container can be used to control the flow of solution streaming from the container through the nozzle. The pump can be programmed to increase or decrease the flow at different points during electrospinning.

The electrospinning occurs due to the presence of a charge in either the orifices or the target, while the other is grounded. In some embodiments, the nozzle or orifice is charged and the target is grounded. Those of skill in the electrospinning arts will recognize that the nozzle and solution can be grounded and the target can be electrically charged.

The target can also be specifically charged or grounded along a preselected pattern so that the solution streamed from the orifice is directed into specific directions. The electric field can be controlled by a microprocessor to create an electrospun matrix having a desired geometry. The target and the nozzle or nozzles can be engineered to be movable with respect to each other thereby allowing additional control over the geometry of the electrospun matrix to be formed. The entire process can be controlled by a microprocessor that is programmed with specific parameters that will obtain a specific preselected electrospun matrix.

Minimal electrical current is involved in the electrospinning process, therefore the process does not denature the materials that form the electrospun matrix, because the current causes little or no temperature increase in the solutions during the procedure.

The degree of branching can be varied by many factors including, but not limited to, voltage (for example ranging from about 0 to 30,000 volts), distance from a syringe tip to the substrate (for example from 1-100 cm, 0-40 cm, and 1-10 cm), the speed of rotation, the shape of the mandrel, the relative position of the a syringe tip and target (i.e. in front of, above, below, aside etc.), and the diameter of a syringe tip (approximately 0-2 mm), and the concentration and ratios of compounds that form the electrospun matrix. Other parameters which are important include those affecting evaporation of solvents such as temperature, pressure, humidity. The molecular weight of the polymer improves its ability to entangle and form fibers, and polymers with the molecular weight of 100 kDa generally performed. Those skilled in the art will recognize that these and other parameters can be varied to form electrospun materials with characteristics that are particularly adapted for specific applications.

The geometry of the grounded target can be modified to produce a desired matrix. By varying the ground geometry, for instance having a planar or linear or multiple points ground, the direction of the streaming materials can be varied and customized to a particular application. For instance, a grounded target comprising a series of parallel lines can be used to orient electrospun materials in a specific direction. The grounded target can be a cylindrical mandrel whereby a tubular matrix is formed. The ground can be variable surface that can be controlled by a microprocessor that dictates a specific ground geometry that is programmed into it.

Electrospinning allows great flexibility and allows for customizing the construct to virtually any shape needed. In shaping matrices, portions of the matrix may be sealed to one another by, for example, heat sealing, chemical sealing, and application of mechanical pressure or a combination thereof.

The various properties of the electrospun materials can be adjusted in accordance with the needs and specifications of the cells to be suspended and grown within them. The porosity, for instance, can be varied in accordance with the method of making the electrospun materials or matrix. Electrospinning a particular matrix, for instance, can be varied by fiber size and density. If the cells to be grown in the matrix require a high nutrient flow and waste expulsion, then a loose matrix can be created. On the other hand, if the tissue to be made requires a dense environment, then a dense matrix can be designed.

One embodiment for appropriate conditions for electrospinning a matrix is as follows. For electrospinning a matrix by combining 45% collagen I, 15% elastin and 40% PLGA, the appropriate approximate ranges are: voltage 0-30,000 volts (10-100 kV potential preferably 15-30 kV); pH 7.0 to 8.0; temperature 20 to 40° C., e.g., room temperature of 25° C.; and the distance from the container to the grounded plate can range from about 1 cm to about 100 cm, preferably about 1 cm to 10 cm. In addition to depositing the charged fibers on the grounded plate, the fibers can be deposited onto another substrate such as a stainless steel mandrel. The mandrel can be rotated at 20-1000 rpm, preferably about 300-700 rpm.

The electrospun nanofibers used in the methods and compositions of the invention can be natural or synthetic. In one embodiment, the electrospun nanofibers are comprised of natural polymers. Exemplary natural polymers include cellulose acetate (CA), chitin, chitosan, collagen, cotton, dextran, elastin, fibrinogen, gelatin, heparin, hyaluronic acid (HA), poly 3-hydroxybutyrate-co-3-hydroxyvalerate (PHBV), regenerated cellulose (RC), silk, and zein.

In one embodiment, the electrospun nanofibers are made of degradable or non-degradable synthetic polymer material. Exemplary degradable polymers include poly(ε-caprolactone) (PCL), poly(ε-caprolactone-co-ethyl ethylene phosphate) (PCLEEP), poly(lactic acid) (PLA), poly(lactic-co-glycolic acid) (PLGA), poly(lactic acid-co-ε-caprolactone) (PLACL), and polydioxanone (PDO). Exemplary non-degradable polymers include poly acrylamide (PAAm), poly acrylic acid (PAA), poly acrylonitrile (PAN), poly amide (Nylon) (PA, PA-4,6, PA-6,6), poly aniline (PANI), poly benzimidazole (PBI), poly bis(2,2,2-trifluoroethoxy) phosphazene, poly butadiene (PB), poly carbonate (PC), poly ether amide (PEA), poly ether imide (PEI), poly ether sulfone (PES), poly ethylene (PE), poly ethylene-co-vinyl acetate (PEVA), poly ethylene glycol (PEG), poly ethylene oxide (PEO), poly ethylene terephthalate (PET), poly ferrocenyldimethylsilane (PFDMS), poly 2-hydroxyethyl methacrylate (HEMA), poly 4-methyl-1-pentene (TpX), poly methyl methacrylate (pMMA), poly p-phenylene terephthalamide (PPTA), poly propylene (PP), poly pyrrole (PPY), poly styrene (PS), polybisphenol-A sulfone (PSF), poly sulfonated styrene (PSS), Styrene-butadiene-styrene triblock copolymer (SBS), poly urethane (PU), poly tetrafluoro ethylene (PTFE), poly vinyl alcohol (PVA), poly vinyl carbazole, poly vinyl chloride (PVC), poly vinyl phenol (PVP), poly vinyl pyrrolidone (PVP), and poly vinylidene difluoride (PVDF). A preferred synthetic polymer is polyethersulfone (PES).

The electrospun nanofiber compostions of the invention can be made of any one of polymers identified herein. The electrospun nanofiber compostions of the invention can also be made of any combination of the polymers identified herein.

Electrospun matrices can be formed of electrospun fibers of synthetic polymers that are biologically compatible. The term "biologically compatible" includes copolymers and blends, and any other combinations of the forgoing either together or with other polymers. The use of these polymers will depend on given applications and specifications required. A more detailed discussion of these polymers and types of polymers is set forth in Brannon-Peppas, Lisa, "Polymers in Controlled Drug Delivery," Medical Plastics and Biomaterials, November 1997, which is incorporated herein by reference.

The compounds to be electrospun can be present in the solution at any concentration that will allow electrospinning. In one embodiment, the compounds may be electrospun are present in the solution at concentrations between 0 and about 1.000 g/ml. In another embodiment, the compounds to be electrospun are present in the solution at total solution concentrations between 10-15 w/v % (100-150 mg/ml or 0-0.1 g/L).

The compounds can be dissolved in any solvent that allows delivery of the compound to the orifice, tip of a syringe, under conditions that the compound is electrospun. Solvents useful for dissolving or suspending a material or a substance will depend on the compound.

By varying the composition of the fibers being electrospun, it will be appreciated that fibers having different physical or chemical properties may be obtained. This can be accomplished either by spinning a liquid containing a plurality of components, each of which may contribute a desired characteristic to the finished product, or by simultaneously spinning fibers of different compositions from multiple liquid sources, that are then simultaneously deposited to form a matrix. The resulting matrix comprises layers of intermingled fibers of different compounds. This plurality of layers of different materials can convey a desired characteristic to the resulting composite matrix with each different layer providing a different property, for example one layer may contribute to elasticity while another layer contributes to the mechanical strength of the composite matrix. These methods can be used to create tissues with multiple layers such as blood vessels.

The electrospun nanofiber has an ultrastructure with a three-dimensional network that supports cell expansion, growth, proliferation, and/or differentiation. This three dimensional network is similar to the environment where many of these stem cells naturally occur, e.g., in bone marrow. The spatial distance between the fibers plays an important role in cells being able to obtain nutrients for growth as well as for allowing cell-cell interactions to occur. Thus, in various embodiments of the invention, the distance between the fibers may be about 50 nanometers, about 100 nanometers, about 150 nanometers, about 200 nanometers, about 250 nanometers, about 300 nanometers, about 350 nanometers, about 600 nanometers, about 750 nanometers, about 800 nanometers, about 850 nanometers, about 900 nanometers, about 950 nanometers, about 1000 nanometers (1 micron), 10 microns, 10 microns, 50 microns, about 100 microns, about 150 microns, about 200 microns, about 250 microns, about 300 microns, about 350 microns, about 400 microns, about 450 microns, or about 500 microns. In various embodiments the distance between the fibers may be less than 50 nanometers or greater than 500 microns and any length between the quoted ranges as well as integers.

Additionally, in various embodiments of the invention, the fibers can have a diameter of about 50 nanometers, about 100 nanometers, about 150 nanometers, about 200 nanometers, about 250 nanometers, about 300 nanometers, about 350 nanometers, about 600 nanometers, about 750 nanometers, about 800 nanometers, about 850 nanometers, about 900 nanometers, about 950 nanometers, about 1000 nanometers (1 micron), 50 microns, about 100 microns, about 150 microns, about 200 microns, about 250 microns, about 300 microns, about 350 microns, about 400 microns, about 450 microns, or about 500 microns, or the diameter may be less than 50 nanometers or greater than 500 microns and any diameter between the quoted ranges as well as integers. A preferred fiber diameter is between 100-700 nm.

The pore size in an electrospun matrix can also be controlled through manipulation of the composition of the material and the parameters of electrospinning. In some embodiments, the electrospun matrix has a pore size that is small enough to be impermeable to one or more types of cells. In one embodiment, the average pore diameter is about 500 nanometers or less. In another embodiment, the average pore diameter is about 1 micron or less. In another embodiment, the average pore diameter is about 2 microns or less. In another embodiment, the average pore diameter is about 5 microns or less. In another embodiment, the average pore diameter is about 8 microns or less. Some embodiments have pore sizes that do not impede cell infiltration. In another embodiment, the matrix has a pore size between about 0.1 and about 100 $\mu m^2$. In another embodiment, the matrix has a pore size between about 0.1 and about 50 $\mu m^2$. In another embodiment, the matrix has a pore size between about 1.0 µm and about 25 µm. In another embodiment, the matrix has a pore size between about 1.0 µm and about 5 µm.

The mechanical properties of the matrix or core will depend on the polymer molecular weight and polymer type/mixture. It will also depend on orientation of the fibers (preferential orientation can be obtained by changing speed of a rotating or translating surface during the fiber collection process), fiber diameter and entanglement. The cross-linking of the polymer will also effect its mechanical strength after the fabrication process. The electrospun nanofiber core can be comprised of parallel or randomly oriented fibers.

In certain embodiments of the invention, a polymer is grafted onto the electrospun nanofiber core. Exemplary polymers that can be grafted onto the electrospun core include, but are not limited to, polymers having functional groups which can be initiated by free radicals, e.g., free radicals formed on the surface of the electrospun core. Exemplary grafted polymers include poly(acrylic acid) and derivatives and copolymers thereof, e.g., polymethacrylic acid and poly(acrylic acid-co-hydroxyethylmethacrylic acid), polyallylamine and derivatives and copolymers thereof.

In further embodiments of the invention the polymers grafted on the electrospun nanofiber core are derivatized. In general, the polymers are derivatized so that cells, e.g., stem cells, are better able to interact with the compositions of the invention. In one embodiment, the polymers are derivatized to have a positive charge. In another embodiment, the polymers are derivatized to have a negative charge. Exemplary derivatives include carboxylic, hydroxyl and amino moieties.

In other embodiments, the polymers are derivatized with a biological agent, e.g., a nucleic acid, peptide or polypeptide. In exemplary embodiments, the peptide or polypeptide is a cell adhesion peptide or heparin.

In yet further embodiments, the compositions of the invention comprise a spacer molecule between the electrospun nanofiber and the derivatized moiety. The spacer molecule can allow for improved functionality of the compositions of the invention. In exemplary embodiments, the spacer is a ethylene, propylene, butylenes, hexylene moiety.

The invention further provides methods for expanding and differentiating stem cells using the compositions described herein.

The methods involve contacting stem cells with the compositions of the invention for a time and under conditions that allow for expansion and/or differentiation of the stem cells. The electrospun nanofiber compositions of the invention can be tailored for the type of stem cell being used. For example, the nanofiber compostions can be derivatized with moieties or peptides that increase the association of a given type of stem cell with the composition. For example, the composition can be derivatized with positively charged moieties to bind hematopoetic stem cells.

The invention further provides methods and compositions to produce lineage committed cells from stem cells. Specifically, and as set forth in the examples, the instant invention provides methods for producing erythrocyte committed cells from hematopoietic stem cells. without being bound by theory, it is likely that the compositions of the invention mimic at least a portion of the bone marrow stem cell niche function. Specifically, cells expanded and differentiated using this method showed a higher percentage of erythrocyte committed cells in the soluble fraction of the cells when compared to the cells that remain bound to the composition. Accordingly, isolating the soluble fraction allows one to collect a enriched population of erythrocyte committed cells.

The stem cells made by the methods of the invention can be used for research and therapeutic uses.

EXAMPLES

It should be appreciated that the invention should not be construed to be limited to the examples that are now described; rather, the invention should be construed to include any and all applications provided herein and all equivalent variations within the skill of the ordinary artisan.

Methods of the Invention

The results reported herein were obtained using the following Materials and Methods:

Electrospinning of Polyethersulfone Nanofiber Mesh

All chemicals were purchased from Sigma-Aldrich (USA) unless otherwise stated. Polyethersulfone (PES) granules (Mw: 55,000) was purchased from Goodfellow Cambridge Limited (UK). PES pellets were dissolved in dimethylsulfoxide (DMSO) at 20 wt % concentration and placed in a plastic syringe fitted with a 27G needle. A syringe pump (KD Scientific, USA) was used to feed the polymer solution into the needle tip. The feed rate of the syringe pump was fixed at 0.3 mL/h. The PES nanofiber meshes were fabricated by electrospinning at 13 kV using a high voltage power supply (Gamma High Voltage Research, USA). Nanofibers were collected directly onto grounded 15 mm diameter glass coverslips (Paul Marienfeld, Germany) located at a fixed distance of 160 mm from the needle tip, over a collection time of 25 min. PES films were fabricated by dip-coating glass in 10 wt % PES in DMSO. The deposited nanofiber and film samples were washed thoroughly in distilled water and then in ethanol to remove any residue DMSO, and subsequently dried and stored in a desiccator.

Surface Grafting of PES Nanofiber Mesh with Poly(Acrylic Acid)

Acrylic acid (AAc) (Merck, Germany) was distilled and stored at −20° C. prior to use. Poly(acrylic acid) (PAAc) was grafted onto the PES nanofiber mesh surface by photo-polymerization, as described previously with slight modification on the grafting conditions (Chua et al. (2005) Biomaterials 26:2537-47). Briefly, samples were immersed in aqueous solution containing 3% AAc solution and 0.5 mM NaIO4 in a flat-bottom glass container. The temperature of the solution was maintained at 8° C. by cooling the container in a cold-water bath. The samples were then exposed to UV from a 400 W mercury lamp (5000-EC, Dymax, Germany) for 2 min at a distance of 25 cm. The PAAc-grafted meshes were then thoroughly washed with deionized water at 37° C. for over 36 h to remove any ungrafted PAAc from the surface of the scaffold and dried in a storage desiccator.

Amination of PAAc-Grafted PES Nanofiber Mesh and Films

The PAAc-grafted PES nanofiber mesh and films were further conjugated with ethylene diamine (EtDA) using a 2-step carbodiimide cross-linking method. Briefly, each scaffold was first gently shaken in 2 mL acetonitrile containing 50 mM N-hydroxysuccinimide (NHS) and 50 mM dicyclohexylcarbodiimide (DCC). After 6 hours, the reaction solution was carefully aspirated and each scaffold was immediately immersed into 2 mL acetonitrile containing 0.03 mmol EtDA. After 12 hours, the reaction solution was carefully aspirated and each scaffold was thoroughly washed in absolute ethanol to remove any dicyclohexyl urea (DCU), which is a by-product of the conjugation reaction. As a control, several PAAc-grafted PES nanofiber meshes were hydroxylated instead, by conjugation with ethanolamine using the same modification protocol as described above. All substrates were subsequently sterilized in 70% ethanol, then loaded into 24-well tissue culture plates (Nunc) and stored in sterile PBS until use.

Surface Analysis of Modified PES Nanofiber Mesh and Films

Surface amine density was quantified according to the method described by Kakabakos et al. (1994) Biomaterials (15:289-97). Briefly, primary amino groups on the substrates were first converted to sulfhydryl groups through reaction with excess 2-iminothiolane (Pierce, USA). The surface sulfhydryl groups were then determined using a BCA assay kit (Pierce) using L-cysteine to generate a standard curve. Surface wettability of the various substrates was characterized by measuring the water contact angle at room temperature using a video contact angle goniometer (Advanced Surface Technology, USA). Samples of unmodified and aminated PES nanofiber meshes were also imaged using a field emission scanning electron microscope (FESEM, FEI Company, USA) for detection of any morphology changes caused by the entire amination process. Fiber diameters were measured by analyzing representative SEM mages of nanofibers using NIH ImageJ software (http://rsb.info.nih.gov/ij/). At least 250 measurements were recorded for each analysis.

Ex Vivo Hematopoietic Expansion Cultures

Frozen human umbilical cord blood CD34+HSPCs were purchased from AllCells, USA (San Mateo, Calif.), which were obtained from normal volunteers participating in an Institute Reviewing Board (IRB) approved donor program (AllCells). The CD34+ purity in the HSPC was determined to be 98% by flow cytometry and the viability was determined to be >97% by Trypan blue. Purified recombinant human stem cell factor (SCF), Flt-3 ligand (Flt3), thrombopoietin (TPO) and IL-3 was purchased from Peprotech Inc., (Rocky Hill, N.J., USA). The StemSpan SFEM medium, MethoCult GF+ H4435 and MyeloCult H5100 were all from StemCell Technologies (Vancouver, BC, Canada).

Different substrates were secured at the bottoms of wells of a 24-well tissue culture plate. Six hundred HSPCs were seeded onto each scaffold in 0.6 mL StemSpan™ serum-free expansion medium, which consists of 1% BSA, 0.01 mg/mL recombinant human insulin, 0.2 mg/mL human transferrin, 0.1 mM 2-mercaptoethanol and 2 mM L-glutamine in Iscove's MDM, supplemented with 0.04 mg/mL low density lipoprotein (Athens Research and Technology Inc, USA), 100 ng/mL SCF, 100 ng/mL Flt3, 50 ng/mL TPO and 20 ng/mL IL-3. Cells were cultured at 37° C. in an atmosphere containing 5% CO2 for 10 days without medium change. Similar cultures were also performed on tissue culture polystyrene surface (TCPS), which serve as a positive control in this study. In total, 8 surface conditions were tested: TCPS, PES-(unmodified, carboxylated, aminated) films and PES-(unmodified, carboxylated, hydroxylated, aminated) nanofiber meshes.

Cells were harvested after 10 days of expansion. All substrates were washed once with non-trypsin cell dissociation solution and twice with 2% FBS Hanks' buffer at 5-10 min intervals between each wash. The cell suspensions collected were then concentrated through centrifugation at 500×g for 10 min. Aliquots of the concentrated cells were then used for cell counting by a hematocytometer, flow cytometry analysis, as well as for colony-forming cell assays.

Flow Cytometry

Fluorescently labeled antibodies for CD34 and other cell surface markers (CD13, CD15, CD1 g, CD38, CD45 and GlyA) were purchased from BD Biosciences (USA). Fluorescently labeled antibodies for CD41 were purchased from Dako (USA). The cell samples were incubated at 4° C. for >30 min in 2% FBS Hanks' buffer in the presence of various antibody combinations. After antibody staining, the cells were washed twice using Hanks' buffer and fixed in 1% paraformaldehyde. Cells were analyzed by triple-color flow cytometry on a FACSCalibur analyzer (BD Biosciences). Relevant isotype controls were also included to confirm specificity and for compensation setting. At least 20,000 events were acquired. The Milan-Mulhouse gating method was used for cell enumeration, where a double gating (CD34+ CD45+) strategy was used to identify the primitive hematopoietic progenitor cell population in the ex vivo expansion cultures. The CD34 marker is generally expressed by primitive hematopoietic progenitor cells, while CD45 marker is expressed on all cells of hematopoietic origin with the exception of red blood cells and their immediate precursors.

Colony-Forming Cell (CFC) Assay

Aliquots of expanded cells each scaffold condition in the expansion cultures were suspended into 3.3 mL of MethoCult GF+ H4435 medium (StemCell Technologies) and the cell suspension was plated onto two 35 mm culture dish (1.1 mL each) as instructed in the procedure manual by StemCell Technologies. Duplicate assays are performed for each condition. The culture dishes were then incubated at 37° C., 5% CO2 for 14 days, after which the number of erythropoietic colonies [erythroid burst-forming units (BFU-E)], granulopoietic colonies [granulocyte-macrophage CFU (CFU-GM)], and multilineage colonies (CFU-GEMM) were determined by manual counting under an inverted microscope. Positive colonies are scored on the basis of an accumulation of 20 or more cells. As a control, freshly thawed HSPCs were also evaluated for colony-forming potential.

Scanning Electron Microscopy

Selected cultures samples were gently rinsed with PBS, fixed with 3% glutaraldehyde for 30 min at 20° C., and post-fixed with 1% osmium tetraoxide for another 15 min at 20° C. Samples were then dehydrated using a graded series of ethanol (25%, 50%, 70%, 90%, 95%, 100%, 100%) followed by HMDS drying. The samples were mounted onto aluminum stubs and gold sputter-coated before viewing under FESEM.

Laser Scanning Confocal Microscopy

Selected culture samples were gently rinsed with Hanks' buffer and fixed with 1% formaldehyde for 10 min at 20° C. and immediately washed with 2% FBS Hanks' buffer. Samples were then incubated with PE-labeled CD34 antibodies in 2% FBS Hanks' buffer for >30 min at 4° C. For nuclear staining, Syto16 (Invitrogen, USA) was used. Fluorescent images were taken using a laser confocal microscope (Leica, Germany).

Fabrication of PES Nanofiber Scaffolds

All chemicals were purchased from Sigma-Aldrich (USA) unless otherwise stated. Polyethersulfone (PES) granules (Mw: 55,000) was purchased from Goodfellow Cambridge Limited (UK). PES pellets were dissolved in dimethylsulfoxide (DMSO) at 20 wt % concentration and placed in a plastic syringe fitted with a 27G needle. A syringe pump (KD Scientific, USA) was used to feed the polymer solution into the needle tip. The feed rate of the syringe pump was fixed at 0.3 mL/h. The PES nanofiber meshes were fabricated by electrospinning at 13 kV using a high voltage power supply (Gamma High Voltage Research, USA). Nanofibers were collected directly onto grounded 15 mm diameter glass coverslips (Paul Marienfeld, Germany) located at a fixed distance of 16 cm from the needle tip, over a collection time of 25 min. The deposited nanofiber samples were then washed thoroughly in distilled water and then in ethanol to remove any residual DMSO, and subsequently dried and stored in a desiccator.

Surface Grafting of Scaffolds with Poly(Acrylic Acid)

Acrylic acid (AAc) was distilled and stored at −20° C. prior to use. Poly(acrylic acid) (PAAc) was grafted onto the PES nanofiber mesh surface by photo-polymerization. Samples were immersed in aqueous solution containing 3% AAc solution and 0.5 mM NaIQ4 in a flat-bottom glass container. The temperature of the solution was maintained at 8° C. by cooling the container in a cold-water bath. The samples were then exposed to UV from a 400 W mercury lamp (5000-EC, Dymax, Germany) for 2 min at a distance of 25 cm. The PAAc-grafted meshes were then thoroughly washed with deionized water at 37° C. for more than 36 h to remove any ungrafted PAAc from the surface of the scaffold and dried in a storage desiccator.

Amination of Poly(Acrylic Acid) Grafted Scaffolds

The PAAc-grafted PES nanofiber meshes were further reacted with 1,2-ethanediamine (EtDA), 1,4-butanediamine (BuDA) or 1,6-hexanediamine (HeDA) using carbodiimide cross-linking method. Briefly, each scaffold was first gently shaken in 2 mL acetonitrile containing 50 mM N-hydroxysuccinimide (NHS) and 50 mM dicyclohexylcarbodiimide (DCC). After 6 h, the reaction solution was carefully aspirated and each scaffold was immediately immersed into 2 mL acetonitrile containing 0.03 mmol EtDA, BuDA or HeDA. After 12 h, the reaction solution was carefully aspirated and each scaffold was thoroughly washed in absolute ethanol to remove any dicyclohexyl urea, a by-product of the conjugation reaction. All substrates were subsequently sterilized in 70% ethanol, then loaded into 24-well tissue culture plates (Nunc, Denmark) and stored in sterile PBS until use. Surface characterization and atomic compositions of various PES nanofiber surfaces were determined using x-ray photoelectron spectroscopy (XPS, PHI-1800, Physical Electronics, USA). Binding energies were referenced to the CC/CH2 C(1s) peak at 284.6 eV.

Ex Vivo Hematopoietic Stem/Progenitor Cell Expansion Culture

Frozen human umbilical cord blood CD34+HSPCs were purchased from AllCells, LLC (USA). The CD34+ purity in the post-thawed HSPC was determined to be 98% by flow cytometry and the viability was determined to be more than 97% by Trypan blue. Purified recombinant human stem cell factor (SCF), Flt-3 ligand (Flt3), thrombopoietin (TPO) and IL-3 was purchased from Peprotech Inc. (USA). Low density lipoprotein (LDL) was purchased from Athens Research & Technology Inc. (USA).

Six hundred HSPCs were seeded onto each scaffold. HSPCs were cultured in 0.6 mL StemSpan™ serum-free expansion medium (StemCell Technologies Inc., Canada) supplemented with 0.04 mg/mL LDL, 100 ng/mL SCF, 100 ng/mL Flt3, 50 ng/mL TPO and 20 ng/mL IL-3 at 37° C., 5% $CO_2$ for 10 days. Similar cultures were also performed on tissue culture polystyrene surface (TCPS), which serve as a positive control in this study. In total 6 surface conditions were tested: TCPS, unmodified PES nanofiber mesh (Unmod), carboxylated nanofiber mesh (PAAc), and nanofiber mesh aminated with EtDA, BuDA or HeDA. After 10 days of culture, the expanded cells were harvested and aliquoted according to protocols previously described (Jiang et al. (2006) Biomaterials 27:2723-32; Chua et al. (2006) Biomaterials 27:6043-51). Aliquots of the concentrated cells were then used for cell counting by a hematocytometer, flow cytometry analysis, colony-forming cell (CFC) assay, long-term culture-initiating cell (LTC-IC) assay and mouse engraftment assay.

Flow Cytometry

Cell samples were stained with fluorescently labeled CD13, CD34 and CD45 antibodies (BD Biosciences, USA) according to protocols previously described (Chua et al. (2006) Biomaterials 27:6043-51). Cells were analyzed by flow cytometry (FACSCalibur, BD Biosciences, USA). Relevant isotype controls were also included to confirm specificity and for compensation setting. The Milan-Mulhouse gating method was used for cell enumeration (Gratama et al. (2001) J. Biol. Regul. Homeost. Agents 15:14-22).

Preparation of Culture Samples for Scanning Electron Microscopy (SEM)

Selected culture samples were gently rinsed with PBS, fixed with 3% glutaraldehyde, and post-fixed with 1% osmium tetraoxide. Samples were then dehydrated using a graded series of ethanol followed by hexamethyldisilazane drying. Samples were gold sputter-coated before viewing under field emission scanning electron microscope (FEI Company).

CFC and LTC-IC Assays

For CFC, aliquots of expanded cells from each scaffold condition in the expansion cultures were cultured in two dishes per sample in MethoCult GF+ H4435 medium (StemCell Technologies Inc., Canada). The dishes were then incubated at 37° C., 5% $CO_2$ for 14 days, after which the number of erythropoietic colonies (BFU-E), granulopoietic colonies (CFU-GM) and multilineage colonies (CFU-GEMM) were enumerated with the aid of an inverted microscope and counted by morphologic criteria. For control, freshly thawed HSPCs were also evaluated for colony-forming potential.

For LTC-IC, expanded cells from each scaffold condition in the ex vivo hematopoietic expansion cultures and freshly thawed HSPCs, which serve as controls, were plated onto irradiated M2-10B4 murine fibroblast feeder cells in 35 mm culture dishes and cultured in MyeloCult H5100 medium (StemCell Technologies Inc., Canada). After 5 weeks, cells from each dish were harvested, and cultured according to the CFC assay as described above. LTC-IC numbers were then calculated and normalized according to instructions in the StemCell Technologies procedure manual.

Mouse Engraftment Assay

NOD/SCID mice were maintained and handled at the Biological Resource Center (BRC), Biopolis, Singapore, according to BRC regulations. Six-to-eight-week old mice were irradiated at 350 cGy. Cells harvested from the 10-day ex vivo expansion culture were mixed with 4' 105 irradiated (1,500 cGy) CD34-depleted human bone marrow cells (carrier cells) and injected into mice via the tail vein. As positive controls, two groups of mice received 600 and 20,000 unexpanded HSPCs together with 4' 105 irradiated carrier cells, respectively. A group of irradiated mice were injected with 4' 105 irradiated carrier cells only serve as the negative control. Mice were sacrificed 6 weeks after cell transplantation. Bone marrow cells are harvested and stained with fluorescently labeled human CD45 antibody according to protocols described previously (Feng, Q. et al. (2006) J. Biomed Mater. Res. A. 78:781-91) and analyzed by flow cytometry.

Statistical Analysis

All data were presented as mean±standard deviation. The statistical significance of the data obtained was analyzed by the Student's t-test. Probability values of $p<0.05$ were interpreted as denoting statistical significance.

Example 1

Modification of PES Substrates and Surface Characterization

Figure 1:
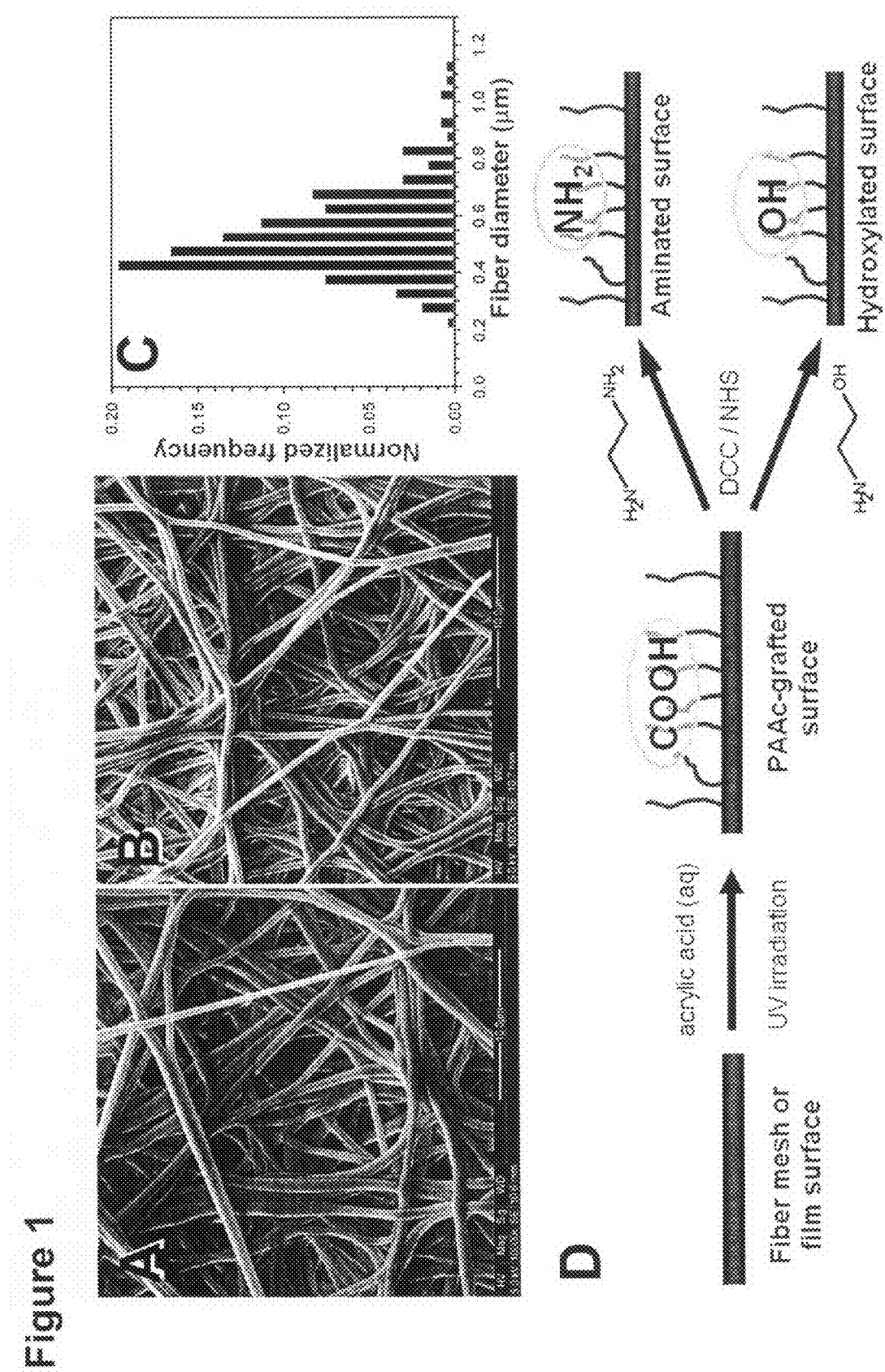
FIG. 1 (A-D) shows SEM images of electrospun PES nanofiber mesh: (A) unmodified; (B) after surface conjugation with ethylenediamine. (C) Fiber diameter distribution profile of PES fibers, electrospun from a 20 wt % PES in DMSO solution (at least 250 measurements taken). (D) PES surface modification scheme.

Nonwoven PES nanofiber meshes were prepared by electrospinning. Parameters that influence the diameter, consistency and uniformity of the electrospun PES fibers included PES concentration in DMSO, applied voltage and needle-collector distance. These parameters were adjusted until unbeaded and uniform fibers could be obtained. The optimal conditions for obtaining such PES nanofiber meshes were described in the Methods section, above. Under the optimized condition, fibers with an average diameter of 529±114 nm were obtained (FIGS. 1A and 1C). PES films were prepared as a 2-D control by dip-coating glass coverslips with a diameter of 15 mm. The film surface exhibited submicron bumps and the average film thickness was 22.5±3.9 mm as analyzed from SEM images of freeze-fractured PES films.

The PES fiber meshes and films were first carboxylated by UV-initiated poly(acrylic acid) grafting. Amino or hydroxyl groups were subsequently introduced to the fiber or film surfaces by reacting ethylenediamine or ethanolamine with the surface carboxylic acid groups using carbodiimide chemistry (FIG. 1D). SEM images comparing unmodified and aminated PES nanofiber mesh (FIG. 1B) did not show any significant morphological difference, indicating that the modification steps did not cause significant degradation/ablation of PES.

Table 1, below, shows characterization of surfaces modified with different functional groups. The results presented in the table show that after PAAc grafting, the contact angle of PES film dropped from 76° to 53°, suggesting an increased surface wettability. The wettability further increased after amination (contact angle was 7° for aminated PES film). The contact angle of the unmodified nanofiber mesh (133°) was higher than PES film (76°). However, the contact angle of PES nanofiber meshes decreased from 133° to 0° after PAAc grafting. Similar observations on the wettability of modified nanofiber surfaces were also reported by Fujihara et al. ((2005) Biomaterials 26:4139-47). After carboxylation, the micropores in the relatively more hydrophilic nanofiber mesh exerted a capillary effect that imbibed the water droplet into the scaffold (Bico, J. et al. (2001) Europhys Lett 55:214-20; Wang et al. (1997) Nature 299:431-2). The aminated and hydroxylated PES fiber meshes also exhibited an un-measurable contact angle (~0°). The density of conjugated primary amino groups on aminated PES nanofiber and film was between 40-60 nmol/cm2, as quantified by the Kakabakos' method (Kakabakos, S E et al. (1994) Biomaterials 15:289-97). All other surfaces showed a background amine density of <5 nmol/cm2. XPS analysis also confirms the presence of nitrogen on aminated surfaces and its absence on unmodified and carboxylated surfaces (data not shown).

TABLE 1

| Surface | Water contact angle (deg.) | Primary amine group density (nmol/cm$^2$) |
|---|---|---|
| TCPS | 56.0 ± 1.4 | 0.4 ± 0.3 |
| PES film | 76.2 ± 5.1 | 0.9 ± 0.5 |
| PES carboxylated film | 52.9 ± 7.3 | 3.4 ± 0.8 |
| PES aminated film | 7.2 ± 2.7 | 50.1 ± 12.5 |
| PES fiber | 133.1 ± 1.8 | 1.3 ± 1.2 |
| PES carboxylated fiber | N.D.* | 4.0 ± 0.0 |
| PES hydroxylated fiber | N.D.* | 1.8 ± 0.8 |
| PES aminated fiber | N.D.* | 56.2 ± 12.6 |

Data shown are means ± SD of triplicate surfaces.
*N.D. The contact angle was too low to be detected Example 2

Ex Vivo HSPC Expansion on Various PES Substrates

Figure 2:
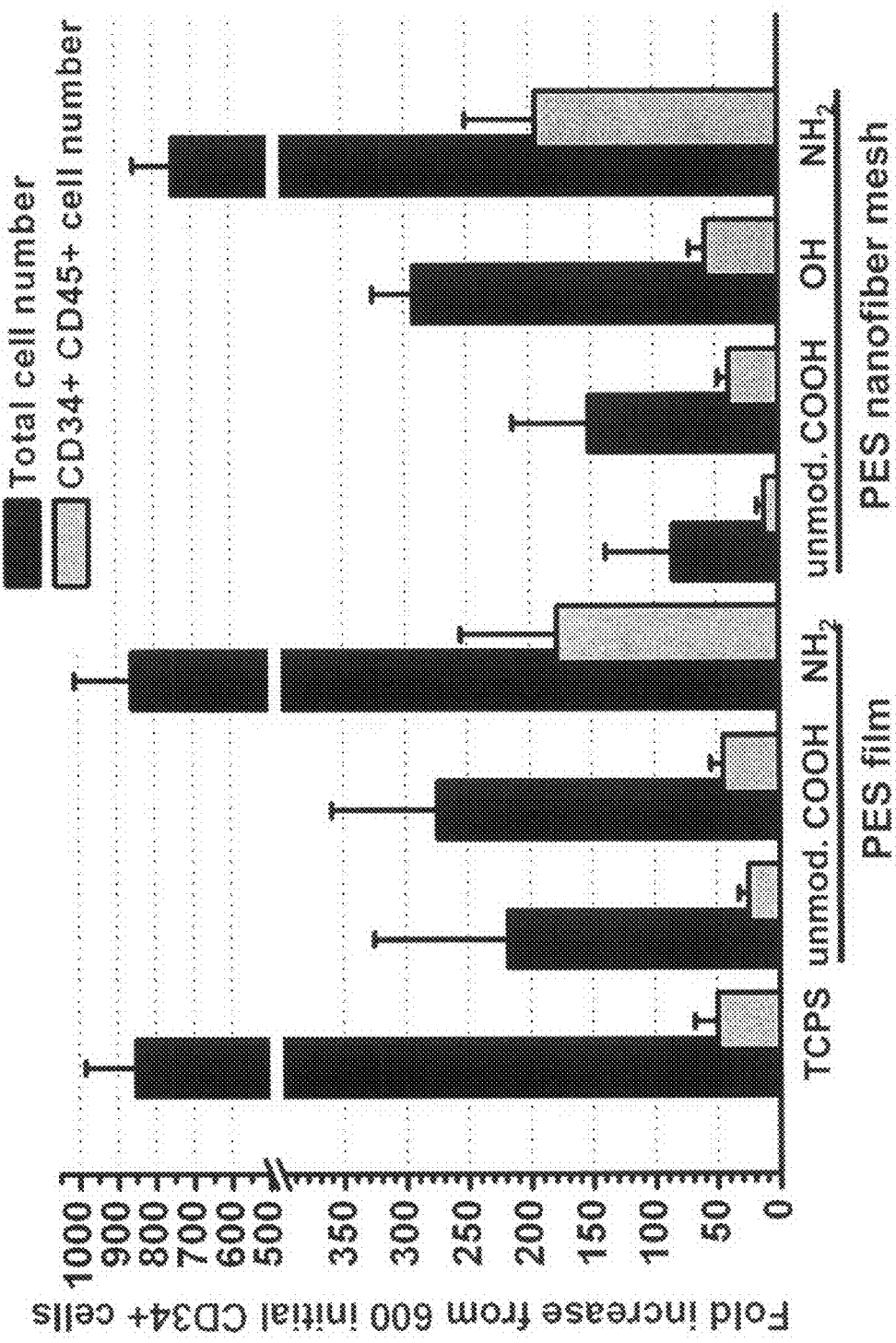
FIG. 2 shows fold expansion of total nucleated cells and CD34+ cells following a 10-day culture of 600 human cord blood HSPCs on different substrates. Total cell numbers were determined by hematocytometer cell counting, while CD34+ cells were determined by FACS analysis at the end of culture.

Next, the efficiency of various substrates (unmodified and modified films and nanofiber meshes) in supporting HSPC expansion was evaluated in a 10-day expansion culture. FIG. 2 shows the total nucleated cell fold expansion and CD34+ CD45+ cell fold expansion after a 10-day expansion culture on different substrates.

Cells harvested from the expansion cultures showed greater than 95% viability in all culture conditions. Noticeable differences were observed in the cell proliferation response of HSPCs to the different substrates. HSPCs cultured on unmodified, carboxylated and hydroxylated PES nanofiber meshes and films yielded low proliferation (85- to 293-fold expansion) of total nucleated cells compared to that cultured on TCPS (850-fold). The CD34+CD45+ cell fraction was between 11.3%-26.1% of total cells as analyzed by flow cytometry, which corresponded to a low (11- to 58-fold) CD34+CD45+ cell expansion. Although HSPCs cultured on TCPS surface proliferated extensively (850-fold), the fraction of CD34+CD45+ cells was only 5.8% of total expanded cells, thus resulting in only about 50-fold expansion of CD34+CD45+ cells. In contrast, the expansion of CD34+ CD45+ cells on aminated film and nanofiber mesh was significantly better than other test groups (p<0.05): aminated PES nanofiber mesh yielded 751-fold expansion of total cells and 195-fold expansion of CD34+CD45+ cells (25.9% of total cells), whereas aminated PES film yielded 859-fold expansion of total cells and 178-fold expansion of CD34+ CD45+ cells (20.8% of total cells). There was no statistically significant difference in fold expansion of CD34+CD45+ cells cultured on aminated PES nanofiber mesh, compared with that on PES film (p>0.05).

Example 3

Clonogenic Assays

CFU assays, shown in FIG. 3, were conducted to evaluate the fraction of primitive progenitor cells in the expanded cultures. Consistent with total and CD34+CD45+ cell expansion results, cells expanded on unmodified, carboxylated and hydroxylated PES nanofiber meshes and films yielded lower total CFU counts (1071±560 to 1996±213) as compared to TCPS (2890±450), aminated PES film (3471±371), and aminated PES nanofiber mesh (3996±358). Interestingly, for aminated PES substrates, a significant difference was observed in the number of more primitive CFU-GEMM units generated by cells expanded on film versus nanofiber mesh with 20% (704/3471) and 28% (1124/3996) of total colony counts, respectively. TCPS on the other hand, generated only 15% (433/2890) CFU-GEMM units. In contrast, TCPS generated relatively higher percentages of CFU-GM units (63%), indicating significant differentiation commitment of the TCPS-expanded cells towards the myeloblast/monoblast lineage, as compared to both aminated PES film and nanofiber scaffold (55% and 49%, respectively, p<0.05 for TCPS vs. PES film, p<0.01 for TCPS vs. PES nanofiber, p>0.05 for PES film vs. PES nanofiber).

Example 4

Surface Marker Expression of Cells Expanded on Various Substrates

The lineage marker expression of the expanded cells was analyzed by flow cytometry (FIG. 4). Only cells expanded on TCPS, aminated PES film and nanofiber mesh, and hydroxylated nanofiber mesh were analyzed because they generated sufficiently high numbers of cells for complete lineage marker expression analysis. Lineage marker expression of freshly thawed, unexpanded cord blood HSPCs was also analyzed as a control. In addition to the definitive human blood progenitor markers which include CD34, CD45 and CD38, the cells were also evaluated for markers for myeloblast/monoblast (CD13, CD15), megakaryoblast (CD41), erythroid (GlyA) and pro-B cell (CD19) lineages.

From these data, the observations can be made: (1) Unexpanded HSPC stocks showed high expression of CD34 (98%), CD45 (99%), CD13 (92%) and CD38 (98%); this is shown in FIG. 4A; (2) Cells expanded on all substrates expressed negligible levels of CD19 (<1%), whereas cell populations expressing CD15, CD41 or GlyA increased (FIG. 4A); (3) Cells expanded on aminated PES nanofiber showed the highest percentage (25.9%) of CD34+CD45+ cells (FIG. 4B); (4) The CD34+CD45+ cell population of expanded cells were primarily negative for CD41, GlyA and CD19 but co-expression of CD13 and CD15 was significant, as shown in FIG. 4C; (5) The CD34+CD45+ fraction of expanded cells displayed lower CD38 co-expression compared to unexpanded cells (FIG. 4C), an effect that had been attributed to serum-free culture condition (Jiang et al. (2006) Biomaterials 27:2723-32; Donaldson et al. (2001) Transplant 27:365-71); (6) The CD34+CD45+ cell population expanded on aminated and hydroxylated PES nanofiber meshes showed lower CD13 expression compared to cells expanded on TCPS and aminated PES film (FIG. 4C).

Example 5

Imaging of Adherent Cells on Aminated Substrates

After 10 days of expansion culture, some samples were processed for SEM and confocal laser microscopy to detect the presence of any adherent cells on these substrates. It was noted that expanded cells adhered weakly to TCPS, unmodified, carboxylated film and nanofiber, and hydroxylated PES nanofiber substrates; and most of these cells could easily be detached with very gentle rinsing. As such, only sparsely scattered cells could be seen under SEM (image not shown). This observation confirmed the weak adhesion of HSPCs on these substrates.

In contrast, on aminated PES nanofiber mesh and film, cell adhesion was evident, although the arrangement of adherent cells on these two substrates appeared to differ greatly, as shown in FIG. 5. On aminated PES nanofiber mesh, approximately 40% cells were adherent following 3 gentle washes; distinct and circular cell colonies were abundant on the mesh (FIG. 5A). Cell colonies ranged from 100 mm to 1.3 mm in diameter, with cells numbering between 50 to a few thousand. In some of the larger colonies, cells could be seen densely packed at the center but thinned out towards the periphery of the colony. At high magnification, the adherent cells could be seen to be anchored via numerous processes in intimate contact with the aminated nanofibers as well as processes from other cells, indicative of cell-fiber and cell-cell interactions (FIGS. 5B & 5C). On aminated film substrates, however, about 25% total cells were adherent, but only sparsely on the surface, compared to adherent cells on aminated nanofiber mesh (FIG. 5D). No discrete cell colony was evident but instead, the adherent cells appeared to align along crevasses (defects generated during film processing) on the surface of the film (FIG. 5E). Most of the adherent cells along the edges of the crevasses sent filopodia into the fissures, as shown in (FIG. 5F). Cells on the smooth surface were washed off.

Prompted by the observation of the unique cell colonies on the surface of aminated nanofiber mesh, next, CD34 antigen expression among the adherent cell population was investigated. Indeed, confocal laser microscope imaging confirmed that a fraction of the cells in the cell colonies showed positive staining with CD34-PE antibody (FIG. 6). Interestingly, the CD34+ cells were located mostly around the peripheries of the cell colonies. Cells at the center of the colonies appeared to be predominantly CD34−. This suggests that HSPCs and the expanded cells were proliferating in an outward, radial manner along the surface of aminated nanofiber mesh, resulting in the formation of circular cell colonies.

Taken together, the data show that the expansion profiles of human umbilical cord HSPCs are evidently different following a 10-day culture on modified and unmodified polymeric substrates with different functional groups and nanofiber topographical cue. Among the carboxylated, hydroxylated, and aminated PES substrates and TCPS, aminated PES substrates mediated the highest expansion efficiency of CD34+ CD45+ cells and CFU potential. Aminated nanofiber mesh could further enhance the HSPC-substrate adhesion and expansion of CFU-GEMM forming progenitor cells.

The experiments presented herein examine the effects of surface functional groups, together with surface topography, on the proliferation and differentiation of HSPCs under a typical expansion condition. The results show that under typical culture conditions, both substrate chemistry (amino vs. hydroxyl vs. carboxyl groups) and topographical features affect the expansion outcome. HSPCs cultured on unmodified, hydroxylated or carboxylated PES substrates exhibited low proliferation. In contrast, HSPCs cultured on aminated PES substrates were able to proliferate as rapidly as those cultured on TCPS, with the advantage that the fold expansion of CD34+ cells on aminated substrates was more than 3.5 times higher than that on commercial TCPS surface; the expanded cells also generated higher numbers of CFU-total and CFU-GEMM counts.

One mechanism to account for the observed effects is that the aminated substrate, being positively charged, selectively enrichs certain protein components from the medium, which then contribute to the expansion outcome (Keselowsky, B. G. et al. (2004) Biomaterials 25:5947-54; Kakabakos S. E. et al. (1994) Biomaterials 15:289-97; and Gratama, J. W. et al. (2001) J. Biol. Regul. Homeost. Agents 15:14-22). Another mechanism by which aminated surface enhanced HSPC expansion and CD34+ phenotype maintenance is by direct interaction with the HSPCs through their surface CD34 antigen. CD34 antigen is a highly sialylated and negatively charged glycophosphoprotein, and its expression decreases as HSPCs become differentiated (Krause, D. S. et al. (1996) Blood 87:1-13; Lanza, F. et al (2001) J. Biol. Regul. Homeost. Agents 15:1-13).

Taken together, the data presented herein indicates that aminated substrate may play a role in facilitating HSPC proliferation and/or maintenance of the HSPC phenotype, and underscores the importance of culture substrate in influencing the proliferation and differentiation of HSPCs.

Example 6

Surface Characterization of Aminated Nanofiber Scaffolds

Nonwoven PES nanofiber meshes with an average diameter of 529±114 nm were prepared by electrospinning process. The PES nanofiber meshes were first carboxylated by UV-initiated PAAc grafting and subsequently reacted with diamines with 2, 4, or 6 carbon spacers (EtDA, BuDA or HeDA respectively) using carbodiimide cross-linking chemistry. XPS analysis showed that surface nitrogen abundance on the aminated fibers was between 11.6%-13.4%, shown in FIG. 7 and Table 2, shown below, which indicated similar conjugation efficiencies of amino groups on different nanofiber surfaces. The unmodified and PAAc-grafted fibers, on the other hand, showed a background surface nitrogen abundance of less than 0.2%.

TABLE 2

| PES nanofiber scaffolds | C atomic abundance (%) | O atomic abundance (%) | N atomic abundance (%) | S atomic abundance (%) |
|---|---|---|---|---|
| Unmodified | 74.2 | 20.2 | 0.2 | 5.4 |
| PAAc-grafted | 68.6 | 27.7 | 0.1 | 3.6 |
| EtDA-conjugated | 65.2 | 19.8 | 13.4 | 1.6 |
| BuDA-conjugated | 67.9 | 17.5 | 13.2 | 1.4 |
| HeDA-conjugated | 71.8 | 14.9 | 11.6 | 1.7 |

In addition, the carbon XPS spectra (C1s) showed that following PAAc grafting, the weak $\pi \rightarrow \pi^*$ shake-up satellite peak at 291.7 eV (attributed to aromatic carbon species in PES) was absent, and replaced by the characteristic O—C=O peak from grafted PAAc chains (FIG. 7). Subsequently, C1s spectra of amine-conjugated nanofiber meshes showed the absence of O—C=O peak, indicating the complete conversion of surface PAAc carboxylic acid groups to amide groups during the amination reaction.

Example 7

Ex Vivo HSPC Expansion on Aminated Nanofiber Scaffolds

The efficiency of nanofiber scaffolds on supporting HSPC expansion was evaluated through a 10-day expansion culture. FIG. 8 shows the fold expansions of total nucleated cells and CD34+CD45+ cells cultured on aminated nanofiber scaffolds with different spacers and control surfaces. Cells harvested from the expansion culture showed over 95% viability in all culture conditions. HSPCs cultured on unmodified and PAAc-grafted nanofibers yielded the lowest proliferation of total nucleated cells (85- and 152-fold, respectively) with 13.3% and 26.1% CD34+CD45+ cells among expanded cells, respectively, corresponding to low expansion efficiencies of CD34+CD45+ cells (11- and 40-fold, respectively). Although HSPCs cultured on TCPS surface proliferated extensively (895-fold), only 5.9% of the expanded cells were CD34+CD45+ cells, corresponding to a 53-fold expansion of CD34+CD45+ cells.

In comparison, expansion efficiencies of CD34+CD45+ cells on all aminated nanofiber meshes were higher than aforementioned test groups: EtDA and BuDA nanofiber meshes resulted in similar expansion profiles (p>0.05) and yielded 773- and 805-fold expansion of total cells (FIG. 8) with 25.9% (200-fold expansion) and 29.2% (235-fold expansion) of CD34+CD45+ cells, respectively (FIG. 9). Overall proliferation of HSPCs on HeDA nanofibers was significantly lower as compared with EtDA and BuDA fiber meshes (210-fold, p<0.05), however, the fraction of CD34+CD45+ cells was the highest at 41.1% of total cells (86-fold CD34+CD45+ cell expansion). An interesting observation was that the CD34+CD45+ cell population expanded on HeDA nanofiber scaffold co-expressed significantly lower level of the myeloid CD13 marker (60.3±7.3% of expanded CD34+CD45+ cell population) compared to EtDA and BuDA nanofiber scaffolds (94.2±3.5% and 92.8±3.8%, respectively, p<0.05, FIG. 3D). The data suggests that substrates that promoted cell adhesion also enhanced the preservation of CD34+CD45+ phenotype and the primitive characteristics of cord blood CD34+ HSPCs. Cell adhesion/retention is known to be a crucial function of the stem cell niche in vivo.

Example 8

Morphology of Adherent Cells on Aminated Scaffolds

SEM imaging was used to monitor the proliferation kinetics of the adherent HSPC population on aminated nanofiber scaffolds. At selected time points during the 10-day expansion culture, samples were processed for SEM to image the adherent cells and their interaction with nanofibers. It has previously been noted that expanded cells adhered weakly to TCPS, unmodified, and PAAc-grafted surfaces. Most of expanded cells were washed off easily with very gentle rinsing (Jiang X S et al. (2006) Biomaterials 27:2723-32; Chua K N et al. (2006) Biomaterials. 27:6043-51); only sparsely scattered cells remained adherent, as visualized by SEM imaging.

Both EtDA and BuDA modified nanofiber meshes mediated significant adhesion. On day 3, small pockets of adherent HSPCs could be observed interacting with and proliferating on these fiber meshes (FIGS. 10A & 10B). The adherent HSPCs were anchored to the aminated nanofibers via numerous uropodia radiating from the cell surface (FIG. 10C). Cells undergoing division were also evident on the nanofiber surface (FIG. 10D). By day 8, the adherent HSPCs proliferated to form distinct, densely populated circular cell colonies on aminated nanofiber meshes (FIGS. 10E & 10F). The distinct circular cell colonies most likely arose from single or small clusters of HSPCs proliferating outwards in a radial manner on nanofiber scaffold. Cell colonies ranged from 0.1 to 1.3 mm in diameter, with cells numbering between fifty to a few thousand. Adherent HSPCs proliferated well on both EtDA (FIGS. 11A & 11B) and BuDA (FIGS. 11C & 11D) nanofiber surfaces to form densely populated cell colonies after 10 days of culture, and this was mirrored by the high mononucleated cell counts (FIG. 8). In contrast, the considerably lower proliferation rate on HeDA modified nanofiber surface (210-fold; FIG. 8) was reflected by smaller colony size, each containing less than 50 cells (FIGS. 11E & 11F). Besides differences in adherent cell density and colony size, no obvious morphological differences could be discerned among the adherent cells expanded on the EtDA, BuDA, or HeDA nanofiber meshes.

Example 9

HSPC Clonogenic Potential from Various Scaffolds

CFC and LTC-IC assays were conducted to evaluate the fraction of primitive progenitor cells in the expanded cultures. The CFC results (FIG. 12A) showed that cells expanded from unmodified and PAAc-grafted nanofiber meshes yielded lower total CFU counts (1199 and 1609, respectively) as compared to TCPS control (2890, p<0.05). Conversely, cells expanded from EtDA, BuDA and HeDA nanofiber meshes yielded significantly higher total CFU counts (3996, 4208 and 3742, respectively) compared to TCPS control (p<0.05). In addition, significant differences were also observed in the number of primitive CFU-GEMM units generated by cells expanded on EtDA, BuDA and HeDA nanofiber meshes; 28.1%, 27.6% and 28.4% of total colony counts, respectively were CFU-GEMM units, compared with that expanded on TCPS (15.0%, p<0.05). TCPS, on the other hand, generated higher percentages of CFU-GM units (63%), indicating stronger differentiation commitment towards the myeloblast/monoblast lineage.

Results from LTC-IC assays (FIG. 12B) suggested that HSPCs expanded from EtDA-, BuDA- and HeDA-scaffolds better preserved the primitive potential than those cultured on control surfaces. LTC-IC counts generated from HSPCs expanded on these fiber scaffolds were significantly higher than that from unexpanded cells (p<0.05), suggesting significant degree of HSPC self-renewal on aminated nanofiber scaffolds. Interestingly, cells expanded from HeDA nanofiber scaffolds generated comparatively high numbers of colony units similar to EtDA and BuDA conditions (FIG. 12), even though the total cell expansion (FIG. 2) was shown to be low. This may be attributed to the relatively high CD34+ phenotype expression of cells expanded on HeDA nanofiber scaffold.

Example 10

NOD/SCID Repopulation Potential of Cells Expanded on Various Scaffolds

To access the effect of surface modified nanofiber scaffolds on the maintenance of the engraftment potential of HSPCs, cells harvested from 10-day expansion cultures were injected intravenously into sub-lethally irradiated NOD/SCID mice together with 4' 105 irradiated carrier cells. As positive controls, 600 and 20,000 ("20k" group in FIG. 13) unexpanded CD34+ cells were also injected into 2 groups of mice. The presence of more than 0.1% of human CD45+ cells among murine bone marrow cells after 6 weeks was used as a criterion for successful primary engraftment in the bone marrow of NOD/SCID mice. Based on this criterion, the groups that yielded positive primary engraftment included cells expanded on EtDA and BuDA scaffolds and 20,000 freshly thawed unexpanded cells (FIG. 7). Moreover, there was statistical significance between EtDA vs. 600 cells and BuDA vs. 600 cells groups (p<0.05), indicating improvement of HSPC engraftment potential following ex vivo expansion on EtDA and BuDA nanofiber scaffolds (600 cells were seeded initially for expansion cultures). Nevertheless, HeDA fiber group failed to show positive engraftment, even though its corresponding CFC and LTC-IC results were comparable to those of EtDA and BuDA groups, suggesting a disjunction between clonogenic and engraftment potential.

Taken together, the results presented herein demonstrate that aminated nanofibers enhance cell-substrate adhesion and ex vivo expansion of HSPCs; and the spacer, through which amino groups were conjugated to nanofiber surface, significantly influenced HSPC adhesion and expansion outcome. The results highlight the importance of scaffold topography and cell-substrate interaction to regulating HSPC proliferation and self-renewal in cytokine-supplemented expansion.

Example 11

HSC Phenotype Maintenance/Self-Renewal Via Nanofiber-Mediated Adhesion

An important implication of this nanofiber-based cell expansion technology is that these functional nanofibers, mimicking part of the bone marrow stem cell niche function, offers a mechanism for HSC phenotype maintenance/self-renewal via nanofiber-mediated adhesion. Cells expanded on this nanofiber niche consist of two distinct populations of cells: those adhere to nanofibers (adherent fraction accounting for ~46% of total expanded cells) and those remained suspension cells (suspension population accounting for ~54% of total expanded cells). The graph shown in FIG. 14 shows cell phenotypic analysis, demonstrating that the adherent population expressed significantly higher percentage of progenitor markers (CD34+CD45+, 43.8%), compared with the non-adherent cell population (21.9%, p<0.05). In contrast, the suspension cell population expressed higher percentage of erythroid marker (46.2% of CD71high, 35.7% of GlyA) than adherent population (14.1% of CD71high, 12.4% of GlyA, p<0.05). The overall percentage of erythroid-committed cells was about 21.5%. CFU assay also indicated significant commitment of the suspension cells towards the erythroid lineage compared to the adherent cells. These characteristics suggest that this nanofiber scaffold provides important outcomes similar to bone marrow niche—cells adhered to nanofibers were maintained in self-renewal cycle; as they detach from nanofibers, cell differentiation was skewed towards erythroid lineage.

The experiments presented herein investigate the effect of covalently grafted amino groups, in conjunction with spacer chain length and surface nanofiber topography, on ex vivo expansion and multipotency maintenance of human umbilical cord HSPCs in cytokine-supplemented serum-free culture. The results confirm that HSPCs expanded on aminated nanofiber scaffolds generated significantly higher numbers of total CFU, CFU-GEMM units and LTC-IC counts, in contrast to those cultured on unmodified and carboxylated nanofiber scaffolds and TCPS substrate. The results highlight the importance of cell-scaffold interactions as a new approach in modulating HSC maintenance and lineage commitment, in addition to cytokine modulations typical used in the literature.

Example 12

Nano-Topographical Cues and Surface-Tethered Biochemical Signals on Expansion and Differentiation of Stem Cells Substrates with nanoscale features have been generated by several techniques including electrospinning (E-spinning), photo-lithography, electron beam etching, nano-phase separation, and reverse nano-imprinting (Yim, E K and Leong, K W. Nanomed.: Nanotech. Biol. Med. (2005)1: 10-21). Among these methods, E-spinning is the most versatile technique, easy to scale up, and applicable for preparing fibers from a wide range of polymers and ceramics (Murugan, R and Ramakrishna, S. Tissue Eng. (2006) 12: 435-447). Currently, it is the only process that has been commercialized. E-spinning can produce continuous fibers of diameters ranging from tens of nanometers to a few microns with random or ordered structure (Li, D and Xia, Y N. Adv. Mater. (2004)16: 1151-1170; Ma, Z W et al. (2005) Tissue Eng. 11 (1-2): 101-109).

Nanofibers generated by E-spinning have been shown to enhance cell adhesion and ECM production in a cell-type specific manner (Yim, E K and Leong, K W. (2005) Nanomed.: Nanotech. Biol. Med. 1 (1): 10-21). Of particular interest, stem cells have also been shown to respond to E-spun nanofibers. For example, human mesenchymal stem cells (hMSCs) cultured on nanofibers facilitated their differentiation into adipogenic, chondrogenic and osteogenic lineages (Li, W J et al. (2005) Biomaterials 26: 5158-5166) and osteogenic culture of hMSCs on nanofibrous scaffolds also promoted cell migration and increased the deposition of endogenously-produced extracellular matrix (Yoshimoto, H et al. (2003) Biomaterials. 24:2077-2082).

Bioactive molecules (e.g. growth factors and cell adhesion molecules) have been incorporated into nanofibers in order to further mimic the functions of natural ECM. A silk nanofiber scaffold encapsulating bone morphogenetic protein-2 and hydroxyapatite nanoparticles has been shown to further enhance the osteogenic differentiation and calcium deposition, compared with silk nanofibers alone (Li, C et al. (2006) Biomaterials. 27 (16): 3115-3124). Nanofibers with surface-tethered galactose ligands mediated specific adhesion to primary rat hepatocytes. These hepatocytes spontaneously infiltrated into fiber mesh and formed stable spheroids and maintained the synthetic phenotype (Chua, K N et al. (2005) Biomaterials. 26: 2537-2547).

Integrating the biochemical cues and topographical cues is important in engineering a functional substrate for stem cell culture. Incorporating specific cell adhesion cues and the capability to enhance the local stability, concentration and presentation of growth factors relevant to hNSC culture is an important feature of an artificial NSC culture substrate. The data presented herein demonstrates a comprehensive approach to systematically incorporate these functionalities into nanofibers, and investigate their roles in hNSC regulation in culture.

Recent work has focused on the development of functionalized nanofibers as a platform to study the effect of nano-topographical cues and surface-tethered biochemical signals on expansion and differentiation of human cord blood hematopoietic stem cells (HSCs) and rat adult neural stem cells (NSCs). The average diameters of the E-spun fibers are in the range of 100 nanometers to a few microns (Chua, K N et al. (2005) Biomaterials. 26: 2537-2547; Chua, K N et al. (2006) Biomaterials. 27: 6043-6051). In order to present the relevant biochemical cues from fiber surfaces in addition to soluble cues added to the medium, a surface grafting method has been developed (Chua, K N et al. (2005) Biomaterials. 26: 2537-2547; Chua, K N et al. (2006) Biomaterials. 27: 6043-6051) to introduce various functional groups to surfaces of a wide range of fibers. This method offers the advantages of high stability of surface functional groups, versatility in achieving wide range of surface concentrations of functional groups (0.1 and 500 nmol/cm2), without compromising fiber integrity.

Aminated E-Spun Nanofibers Enhance Ex Vivo Expansion of Human Umbilical Cord Blood Hematopoietic Stem and Progenitor Cells (HSCs).

Despite the success of bone marrow transplantation in treating a variety of hematological disorders and as a supportive therapy for malignant diseases using autologous and cord blood HSCs, the lack of an effective ex vivo expansion method for HSCs limits the widespread applications of HSC transplantations. It has recently been discovered that E-spun fiber topography and surface biochemical nature synergistically improves the self-renewal, maintenance and engraftment property of human cord blood HSCs.40 A set of aminated nanofibers supported the highest expansion of cryopreserved cord blood CD34+ cells compared with the state-of-art TCPS culture (195-fold vs. 50-fold) and the highest expansion of CFU-GEMM cells (representing more primitive progenitor cells), compared with similarly modified 2-D film and other substrates, as shown in FIG. 15. More interestingly, only on this set of nanofibers was observed selective adhesion of CD34+ cells in unique pattern-abundant adherent colonies, accounting for about 40% of total expanded cells, while about 20% of cells were detected randomly distributed on similarly modified 2-D film, mostly along the cracks.

Nearly half of adherent cells (45±8%) harvested from aminated nanofibers showed CD34+ phenotype, compared to 17±5% in the suspension fraction (FIG. 15*d*). The corresponding percentage of CD34+ cells among adherent and suspension fractions for aminated 2-D film were 21±5% and 17±5%, respectively. This result suggests a selective enrichment effect of HSCs on these nanofibers during expansion—these functionalized nanofibers provided anchorage to HSCs and enhanced HSC phenotype maintenance. HSCs are traditionally expanded in suspension cultures. This is the first direct evidence associating cell-substrate adhesion with HSC phenotype maintenance.

LN-Coated Nanofibers and Fiber Alignment Influence NSC Adhesion, Proliferation and Differentiation.

Before testing FGF-2-tethered nanofibers, the effectiveness of nanofibers coated with cell adhesion molecules on NSC culture was evaluated. A pilot study confirmed that nanofibers coated with laminin (LN), an important ECM component found in ventricular zone basal lamina (Silva, Ga. et al. (2004) Science 303:1352-1355; Adams, D N et al. (2005) J. Neurobiol. 62: 134 147; Campos, L S (2004) Development. 131: 3433-3444) were much more efficient in mediating NSC adhesion and proliferation than collagen- and fibronectin (FN)-coated fibers (data not shown). a PES nanofiber mesh with average diameter of 273±43 nm was used to compare with a PES film (~10 µm thick) prepared by spin-coating; both were coated with polyornithine (PLO)/LN. At saturated coating level, LN-nanofibers as well as the LN-films mediated comparable cell adhesion and total cell proliferation (data not shown). SEM images showed that NSCs cultured on LN-fibers exhibited more rounded morphology in contrast to a flattened morphology on LN-films. A large number of processes were found to extend along nanofiber axes, whereas cells appeared to be more mobile and flattened in single cell form on LN-coated PES film. This is shown in FIG. 16.

This strong cell-fiber interaction prompted us to investigate whether guided alignment of these processes will promote the neuronal differentiation of NSCs. Under differentiation culture (exposure to 0.5% FBS and 0.5 µM retinoic acid), NSCs adhered to aligned LN-coated nanofibers and cells extended processes that grew along the fiber axis, whereas cells exhibited extensive but non-polarized neurite networks on random LN-coated fibers (FIG. 17). Following 6 days of culture, a consistently higher proportion of early neuronal precursors were found on aligned fibers as compared to random fibers, as shown by a higher percentage of Tuj1+ cells observed on aligned nanofibers than on random fibers and TCPS and 2-D film with LN coating. Taken together, aligned nanofibers increased the neuronal differentiation and guide directional growth and process orientation of cultured NSCs.

These results demonstrate that nanofibers provide a unique topographical cue to stem cells in culture. Both the fiber topography and the surface functionality are important factors in influencing cell adhesion, proliferation and differentiation.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A nanofiber composition for the expansion or differentiation of stem cells comprising a core of one or more electrospun polymers, wherein an additional polymer is chemically grafted onto the one or more electrospun polymers, and said one or more electrospun polymers comprise polyethersulfone (PES).

2. The grafted electrospun nanofiber composition of claim 1, wherein the grafted polymer is derivatized.

3. The grafted electrospun nanofiber composition of claim 1, wherein said one or more electrospun polymers further comprise a polymer selected from the group consisting of synthetic polymers, natural polymers, protein engineered biopolymers or combinations thereof.

4. The grafted electrospun nanofiber composition of claim 1, wherein the grafted polymer is poly(acrylic acid) (PAAc).

5. The grafted electrospun nanofiber composition of claim 2, wherein the polymer is derivatized with a positively charged moiety, peptide or polypeptide, cell adhesion peptide or polypeptide, heparin, carboxylic, hydroxyl or amino groups.

6. The grafted electrospun nanofiber composition of claim 2, further comprising a spacer between the grafted nanofiber and the derivatized moiety.

7. The grafted electrospun nanofiber composition of claim 1, comprising poly(acrylic acid) grafted onto a polyethersulfone core.

8. The grafted electrospun nanofiber composition of claim 7, wherein the electrospun fiber composition is aminated.

9. The grafted electrospun nanofiber composition of claim 7, wherein the composition is derivatized with peptides or polypeptides.

10. The grafted electrospun nanofiber composition of claim 9, wherein the composition is derivatized with laminin, heparin, or cell adhesion peptides, or cell adhesion polypeptides.

11. The grafted electrospun nanofiber composition of claim 10, wherein the electrospun composition comprises spacers between the electrospun fiber and the derivatized moiety.

12. The grafted electrospun nanofiber composition of claim 1, wherein the nanofibers are randomly oriented fibers.

13. The grafted electrospun nanofiber composition of claim 1, wherein the electrospun polymers are aligned fibers.

14. The grafted electrospun nanofiber composition of claim 1, wherein the electrospun polymer is produced by uniaxial electrospinning.

15. The grafted electrospun nanofiber composition claim 1, wherein the electrospun polymer is produced by coaxial electrospinning.

16. The grafted electrospun nanofiber composition of claim 1, wherein the electrospun polymer is produced by multiaxial electrospinning.

17. A method for the expansion of a stem cell population comprising:
    contacting a stem cell population with the grafted electrospun nanofiber composition of claims 2;
    thereby expanding the stem cell population.

18. A method for the expansion of a hematopoietic stem/progenitor cell population comprising:
    contacting the stem cell population with the grafted electrospun nanofiber composition of claim 1;
    thereby expanding the stem cell population.

19. A method for the expansion of a embryonic stem cell population comprising:
    contacting the stem cell population with the grafted electrospun nanofiber composition of claim 2;
    thereby expanding the stem cell population.

20. A method for the expansion of a neural stem cell population comprising:
    contacting the stem cell population with the grafted electrospun nanofiber composition of claim 2;
    thereby expanding the stem cell population.

21. A method of producing erythroid committed cells comprising:
    contacting a hematopoietic stem/progenitor cell population with the grafted electrospun nanofiber composition of claim 2;
    isolating the cells in suspension after a time sufficient for expansion and differentiation of the cell population;
    thereby producing erythroid committed cells.

22. A kit for the expansion or differentiation of a stem cell population comprising the grafted electrospun nanofiber composition of claim 2 and instructions for use.

23. The grafted electrospun nanofiber composition of claim 2, wherein the polymer is derivatized with amine groups.

* * * * *